US 12,121,721 B2

(12) United States Patent
DeLancey et al.

(10) Patent No.: US 12,121,721 B2
(45) Date of Patent: Oct. 22, 2024

(54) TRANSVAGINAL TREATMENT OF STRESS URINARY INCONTINENCE

(71) Applicants: HOLOGIC, INC., Marlborough, MA (US); THE REGENTS OF THE UNIVERSITY OF MICHIGAN, Ann Arbor, MI (US)

(72) Inventors: John O. DeLancey, Ann Arbor, MI (US); James Ashton-Miller, Ann Arbor, MI (US); Christian Michael Ulm, Marlborough, MA (US); Jessica Tina Schenck, Marlborough, MA (US)

(73) Assignees: REGENTS OF THE UNIVERSITY OF MICHIGAN, Ann Arbor, MI (US); HOLOGIC, INC., Marlborough, MA (US)

( * ) Notice: Subject to any disclaimer, the term of this patent is extended or adjusted under 35 U.S.C. 154(b) by 197 days.

(21) Appl. No.: 17/702,665

(22) Filed: Mar. 23, 2022

(65) Prior Publication Data

US 2022/0212004 A1 Jul. 7, 2022

Related U.S. Application Data

(63) Continuation of application No. PCT/US2020/055948, filed on Oct. 16, 2020.
(Continued)

(51) Int. Cl.
A61N 1/04 (2006.01)
A61N 1/05 (2006.01)
A61N 1/36 (2006.01)

(52) U.S. Cl.
CPC ....... *A61N 1/36007* (2013.01); *A61N 1/0452* (2013.01); *A61N 1/0524* (2013.01)

(58) Field of Classification Search
CPC . A61N 1/36007; A61N 1/0452; A61N 1/0524
See application file for complete search history.

(56) References Cited

U.S. PATENT DOCUMENTS 4,106,511 A 8/1978 Erlandsson
4,296,760 A 10/1981 Carlsson et al.
(Continued)

FOREIGN PATENT DOCUMENTS

DK 1631211 T3 4/2017
EP 2764888 8/2014
(Continued)

OTHER PUBLICATIONS

PCT International Search Report and Written Opinion for International Appln. No. PCT/US2020/055948, dated Feb. 10, 2021 (11 pages).

*Primary Examiner* — Ankit D Tejani
*Assistant Examiner* — Joshua Brendon Solomon
(74) *Attorney, Agent, or Firm* — MARSHALL, GERSTEIN & BORUN LLP

(57) ABSTRACT

A transvaginal stimulation device comprises a probe body sized to fit entirely within a vaginal cavity of a female patient. The probe body has a stimulating side defined by a length and a width of the probe body. The transvaginal stimulation device further comprises a pair of electrodes disposed on the stimulating side of the probe body and laterally spaced from each other. A method for treating stress urinary incontinence in a female patient comprises inserting the intravaginal device into a vaginal cavity of the female patient, positioning the pair of electrodes against an anterior wall of the vagina of the female patient, and conveying stimulation energy between the pair of electrodes to stimulate at least one muscle of a urethral sphincter muscle of the
(Continued)

female patient without substantially stimulating pelvic floor muscles of the female patient.

15 Claims, 26 Drawing Sheets

Related U.S. Application Data

(60) Provisional application No. 62/924,380, filed on Oct. 22, 2019.

(56) References Cited

U.S. PATENT DOCUMENTS

| | | | |
|---|---|---|---|
| 4,580,578 A | 4/1986 | Barsom |
| 4,881,526 A | 11/1989 | Johnson et al. |
| 5,081,985 A | 1/1992 | Borodulin et al. |
| 5,360,402 A | 11/1994 | Conway et al. |
| 5,370,671 A | 12/1994 | Maurer et al. |
| 5,562,717 A | 10/1996 | Tippey et al. |
| 5,603,685 A | 2/1997 | Tutrone, Jr. |
| 5,618,256 A | 4/1997 | Reimer |
| 5,782,745 A | 7/1998 | Benderev |
| 5,800,501 A | 9/1998 | Sherlock |
| 5,860,940 A | 1/1999 | Schonfeld |
| 5,996,585 A | 12/1999 | Migachyov |
| 6,086,549 A | 7/2000 | Neese et al. |
| 6,110,099 A | 8/2000 | Benderev |
| 6,418,930 B1 | 7/2002 | Fowler |
| 6,432,037 B1 | 8/2002 | Eini et al. |
| 6,460,542 B1 | 10/2002 | James |
| 6,530,879 B1 | 3/2003 | Adamkiewicz |
| 6,659,936 B1 | 12/2003 | Furness et al. |
| 6,685,623 B2 | 2/2004 | Presthus et al. |
| 6,735,474 B1 | 5/2004 | Loeb et al. |
| 6,739,340 B1 | 5/2004 | Jensen et al. |
| 6,741,895 B1 | 5/2004 | Gafni et al. |
| 6,808,485 B2 | 10/2004 | Zunker |
| 6,896,651 B2 | 5/2005 | Gross et al. |
| 7,054,689 B1 | 5/2006 | Whitehurst et al. |
| 7,351,195 B2 | 4/2008 | Farrell |
| 7,771,344 B2 | 8/2010 | Ziv |
| 7,981,021 B2 | 7/2011 | Spitz et al. |
| 8,195,296 B2 | 6/2012 | Longhini et al. |
| 8,360,954 B2 | 1/2013 | Kim |
| 8,369,953 B2 | 2/2013 | Peddicord |
| 8,435,168 B2 | 5/2013 | Ziv et al. |
| 8,509,900 B2 | 8/2013 | Boyd et al. |
| 8,788,040 B2 | 7/2014 | Haessler et al. |
| 8,805,509 B2 | 8/2014 | Boyd et al. |
| 8,818,512 B2 | 8/2014 | Peddicord |
| 8,868,190 B2 | 10/2014 | Guez |
| 8,926,493 B2 | 1/2015 | Karapasha |
| 9,042,987 B2 | 5/2015 | Boyd et al. |
| 9,078,726 B2 | 7/2015 | Karapasha |
| 9,358,383 B2 | 6/2016 | Boyd et al. |
| 9,381,345 B2 | 7/2016 | Boyd et al. |
| 9,393,090 B2 | 7/2016 | Karapasha |
| 9,445,882 B2 | 9/2016 | Henriksson et al. |
| 9,616,226 B2 | 4/2017 | Lockwood et al. |
| 9,656,067 B2 | 5/2017 | Pelger et al. |
| 9,782,583 B2 | 10/2017 | Sharma |
| 9,861,316 B2 | 1/2018 | Egorov |
| 9,950,160 B2 | 4/2018 | Sharma et al. |
| 10,016,599 B2 | 7/2018 | Lockwood et al. |
| 10,238,479 B2 | 3/2019 | Henriksson et al. |
| 2002/0055761 A1* | 5/2002 | Mann ............... A61N 1/36071 607/41 |
| 2005/0228316 A1 | 10/2005 | Morgenstern |
| 2014/0155954 A1* | 6/2014 | Lee ............... A61N 1/36014 607/148 |
| 2020/0101280 A1* | 4/2020 | Peddicord .......... A61N 1/36007 |

FOREIGN PATENT DOCUMENTS

| | | |
|---|---|---|
| EP | 1631211 B1 | 1/2017 |
| EP | 3342453 | 7/2018 |
| JP | 4904156 B2 | 3/2012 |
| WO | WO 1997018857 | 5/1997 |
| WO | WO 00/03659 | 1/2000 |

* cited by examiner

TRANSVAGINAL TREATMENT OF STRESS URINARY INCONTINENCE

RELATED APPLICATION DATA

This patent application is a continuation of International Patent Application No. PCT/US2020/055948, filed Oct. 16, 2020, which claims priority to U.S. provisional application No. 62/924,380, filed Oct. 22, 2019, entitled "TRANSVAGINAL TREATMENT OF STRESS URINARY INCONTINENCE", each of which applications is herein incorporated by reference in its entirety.

FIELD

The present disclosure relates generally to medical devices and techniques for treating stress urinary incontinence.

BACKGROUND

Urethral closure pressure must be greater than urinary bladder pressure, both at rest and during increases in abdominal pressure, to retain urine in the bladder. Measurements of urethral closure pressure using intraurethral catheters have shown that, when a patient is supine, the resting pressure in the bladder neck is about 30 cm H2O, and increases to about 80 cm H2O in a healthy patient approximately halfway along the urethra, after which it decreases to atmospheric pressure at the external meatus of the urethra. Urinary incontinence (UI) occurs when the bladder pressure exceeds the maximum urethral closure pressure, and is one of the most prevalent conditions of the lower urinary tract. The most common type of UI is stress urinary incontinence (SUI), which affects a significant number of people, mostly women. During activities, such as coughing, sneezing, laughing, and exercise, when the bladder pressure increases several times higher than resting urethral pressure, a dynamic process should increase the urethral pressure to enhance urethral closure and thereby maintain urinary continence. SUI occurs when this dynamic process fails, and a sudden increase in the intra-abdominal pressure exceeds the urethral pressure, causing the loss of small amounts of urine.

Currently, there is a large gap in treatment options for SUI between conservative methods (Kegels) and surgical intervention (slings).

Some proposed SUI treatments include the delivery of energy to and/or through the urethral wall by precisely placing an elongated probe having an energy delivery element within the urinary tract, as described in U.S. Pat. No. 9,687,331. These probes can have an anchoring member, such as an inflatable balloon, at a distal portion of the probe that sits in a patient's bladder, and a locking device at the proximal portion of the probe that is placed against the patient's external urethral orifice, urinary meatus and/or adjacent tissue, thereby securing the probe and the energy delivery member in a desirable position within the urethra. These SUI treatments require complicated mechanisms for minimizing movement of the probe relative to the desired treatment site in the urethra and/or paraurethral region, as well as, maintaining patency of the probe lumen. Furthermore, such SUI treatments denature the urethral or paraurethral tissue, and thus, are irreversible.

Other proposed SUI treatments electrically stimulate the nerves, including the sacral nerve or pudendal nerve, as described in U.S. Pat. Nos. 6,449,512, 6,505,074, 6,735,474, 6,836,684, 6,907,209, 6,941,171, 7,047,078, 7,054,689, 7,177,703, 7,343,202, 7,369,894, 7,565,198, and 8,644,938, or stimulate the bladder itself, as described in U.S. Pat. No. 7,769,460; or directly stimulate the pelvic floor or periurethral muscles, as described in U.S. Pat. Nos. 6,354,991, 6,659,936, and 7,613,516. However, these SUI treatments require invasive implantation of the electrodes, as well as the electrical energy source, within the patient.

Still other proposed SUI treatments involve transanally or transvaginally stimulating pelvic floor muscles (e.g., the levator ani) in order to emulate Kegel exercises that strengthen the weakened muscles that were previously thought to cause SUI, as described in U.S. Pat. Nos. 5,370,671 and 6,402,683 due to loss of their supporting function. Stimulation of the pelvic floor muscles, particularly levator ani muscles, is performed in either a clinical setting or home setting using a probe that carries electrodes (e.g., annular electrodes) that non-specifically stimulate the pelvic floor muscles surrounding the vagina or anus. However, in this case, because the electrical stimulation is non-specific, muscles that are not associated with the SUI, in addition to the dysfunctional muscles, are electrically stimulated. Some SUI treatments target only the dysfunctional pelvic floor muscles that cause the SUI by using biofeedback, as described in U.S. Pat. No. 9,656,067. However, these systems require the use of relatively large electrodes and involve a complicated setup. One such system includes an array of electrode patches that extend axially along and circumferentially around a probe to measure electromyography (EMG) signals in the pelvic floor muscles, as well as an external stimulation and control unit, requiring clinical intervention to identify and train the weakened pelvic floor muscles that were thought to cause the SUI.

Research, however, indicates that the main factor causing SUI is weak urethral sphincter muscle(s), rather than a loss of support provided by the pelvic floor muscles or the passive tissue beneath the urethra (see John O. L. Delancey, et al., "Stress Urinary Incontinence: Relative Importance of Urethral Support and Urethral Closure Pressure," The Journal of Urology, Vol. 179, 2286-2290 Jun. 2008; John O. L. Delancey, et al., "Differences in Continence System Between Community-Dwelling Black and White Women With and Without Urinary Incontinence in the EPI Study," American Journal of Obstetrics & Gynecology, 584.e1-584.e2, June 2010). Thus, because levator muscle failure is not a prominent feature of SUI, targeting the pelvic floor muscles for stimulation in order to remedy the loss of support has not been effective. Furthermore, despite the fact that the size and shape of pelvic regions vary greatly between females, prior art electrical stimulation devices designed for the treatment of SUI take a one size fits all solution and, thus, may be completely ineffective for a particular set of females due to an improper fitting between the devices and these females.

Hence there is an ongoing need to provide an improved device and technique that non-invasively electrically stimulates the target anatomical regions associated with SUI with minimal clinical intervention.

SUMMARY

In accordance with the disclosed inventions, a transvaginal stimulation device comprises a probe body sized to fit entirely within a vaginal cavity of a female patient. The probe body has a length extending in a longitudinal direction, a width extending in a lateral direction, and a depth extending perpendicular to the length and width. In one embodiment, the probe body is rigid or semi-rigid, and has a total length having a range of 4 cm-8 cm. In another embodiment, the width of the probe body has a greatest lateral extent that is greater than the depth of the probe body. The probe body has a stimulating side defined by the length and the width of the probe.

The transvaginal stimulation device further comprises a pair of electrodes (e.g., a transverse pair of electrodes) disposed on the stimulating side of the probe body and laterally spaced from each other. In one embodiment, the transvaginal stimulation device is free of any electrodes laterally disposed relative to the pair of electrodes. In another embodiment, the probe body has a non-stimulating side opposite the stimulating side of the probe body, in which case, the non-stimulating side of the probe body is free of any electrode. In still another embodiment, the pair of electrodes each have an elongated shape and are disposed parallel to each other, and may respectively have lengths extending along the length of the probe body in a range of about 4 mm-12 mm.

In one embodiment, the transvaginal stimulation device further comprises stimulation circuitry contained within the probe body. The stimulation circuitry is configured for delivering bipolar electrical stimulation energy between the pair of electrodes. In another embodiment, the transvaginal stimulation device further comprises a user interface disposed on the probe body. The user interface is configured for deactivating the stimulation circuitry.

A transvaginal stimulation system may comprise the transvaginal stimulation device set forth above, a clinician programmer configured for wirelessly programming the transvaginal stimulation device, and a patient control configured for wirelessly controlling operation of the transvaginal stimulation device.

In accordance with a first aspect of the disclosed inventions, the probe body has a concave region longitudinally extending along the stimulating side of the probe body. In this case, the pair of electrodes disposed on the stimulating side of the probe body and laterally spaced from each other, such that the concave region is disposed between the pair of electrodes. In one embodiment, the concave region is shaped to cradle a urethra carina of the female patient when the probe body is positioned in a vaginal cavity of the female patient.

In accordance with another aspect of the disclosed inventions, the pair of electrodes have an edge-to-edge lateral spacing in the range of 5 mm-25 mm. In one embodiment, the pair of electrodes have an edge-to-edge lateral spacing in the range of 10 mm-20 mm.

In accordance with yet another aspect of the disclosed inventions, a distal region of the probe body laterally flares outward in a distal direction from a mid-region of the probe body to form a flattened scoop. In one embodiment, the flattened scoop angles away from the stimulating side of the probe body. In another embodiment, a proximal region of the probe body laterally flares outward in a proximal direction from the mid-region to form shoulders. In this case, the mid-region of the probe body may be sized and configured, such that when the probe body is fully disposed in the vaginal cavity, levator ani muscles of the female patient are disposed adjacent to the mid-region between the flattened scoop and the shoulders.

In accordance with still another aspect of the disclosed inventions, the transvaginal stimulation device further comprises an extraction element extending proximally from the probe body configured for being grasped to extract the probe body from the vaginal cavity of the female patient. In one embodiment, the extraction mechanism comprises a finger-hold having a proximal surface configured for approximating a pubic bone of the female patient when the probe body is fully disposed in the vaginal cavity of the female patient.

In accordance with yet another aspect of the disclosed inventions, the pair of electrodes includes a first electrode having a first flat tissue contacting surface and a second electrode having a second flat tissue contacting surface tissue. In this case, the first tissue contacting surface and the second tissue contacting surface form an angle within the range of 160°-200°, preferably in the range of 170°-190°. In one embodiment, the first tissue contacting surface and the second tissue contacting surface form an angle of 180°.

In accordance with a still further aspect of the disclosed inventions, the pair of electrodes are respectively positioned on the probe body, so that when the probe body is positioned in a vaginal cavity of the female patient, bipolar electrical stimulation energy delivered between the pair of electrodes to stimulate at least one muscle of a urethral sphincter (e.g., the mid-urethral striated sphincter muscle) of the female patient without substantially stimulating pelvic floor muscles of the female patient.

In accordance with yet another aspect of the disclosed inventions, the transvaginal stimulation device further comprises a pair of linear electrode arrays extending along the length of the probe body. In one embodiment, different subsets of electrodes of the respective pair of electrodes arrays are configured for being selectively activated. The subsets of electrodes may, e.g., comprise different bipolar pairs of electrodes, such as transverse bipolar pairs of electrodes or longitudinal bipolar pairs of electrodes. In another embodiment, the different subsets of electrodes are configured for being cyclically activated one-at-a-time. In still another embodiment, a clinician programmer is configured for determining a stimulation regimen by selectively activating different pairs of electrodes respectively in the linear electrode arrays, and programming the transvaginal stimulation device with the stimulation regimen, such that the transvaginal stimulation device is configured for conveying electrical stimulation energy between the pair of electrodes in accordance with the stimulation regimen.

In accordance with still another aspect of the disclosed inventions, a proximal region of the probe body comprises shoulders that laterally taper inward in a proximal direction to form a waist. An axial center of the pair of electrodes may be distally spaced from the waist a distance in the range of 1.5 cm-2.5 cm. In one embodiment, the probe body comprises telescoping proximal and distal probe bodies configured for being axially displaced relative to each other, such that a distance between the pair of electrodes and the waist of the probe body can be varied. In another embodiment, the pair of electrodes is configured for being axially displaced relative to the probe body, such that a distance between the pair of electrodes and the waist of the probe body can be varied.

In accordance with yet another aspect of the disclosed inventions, a method for treating stress urinary incontinence in a female patient using the transvaginal stimulation device comprises inserting the intravaginal device into a vaginal cavity of the female patient. If the probe body has a concave region longitudinally extending along the probe body, the method can further comprise cradling a urethra carina of the female patient when the probe body is inserted in the vaginal cavity of the female patient. If the width of the probe body has a greatest lateral extent that is greater than the depth of the probe body, the method may further comprise preventing rotation of the probe body relative to the vaginal cavity of the female patient. If the distal region of the probe body laterally flares outward in a distal direction from a mid-region to form a flattened scoop, and the proximal region of the probe body laterally flares outward in a proximal direction from mid-region to form shoulders, the levator ani muscles of the female patient may be disposed adjacent to the mid-region between the flattened scoop and the shoulders when the probe body is fully disposed in the vaginal cavity. If the flattened scoop angles away from the stimulating side of the probe body, the flattened scoop may conform to a posteriorly angled cranial end of the vaginal cavity of the female patent when the probe body is fully disposed in the vaginal cavity.

In one embodiment, the method further comprises positioning the pair of electrodes against an anterior wall of the vagina of the female patient, and conveying stimulation energy between the pair of electrodes to stimulate at least one muscle of a urethral sphincter muscle (e.g., a mid-urethral striated sphincter muscle) of the female patient without substantially stimulating pelvic floor muscles of the female patient. In one method, the stimulation energy is unidirectionally conveyed through an anterior wall of a vagina of the female patient to stimulate the urethral sphincter muscle of the female patient.

In one embodiment, the method further comprises measuring a urethral closing pressure of the female patient while applying the stimulation energy to the urethral sphincter muscle of the female patient in accordance with a stimulation regimen, and controlling the stimulation regimen in response to the measured urethral closing pressure. Controlling the stimulation regimen may comprise determining a stimulation regimen by selectively activating different pairs of electrodes arranged in a pair of linear electrode arrays extending along the length of the probe body, and programming the transvaginal stimulation device with the stimulation regimen, such that the transvaginal stimulation device is configured for conveying the electrical stimulation energy between the pair of electrodes in accordance with the optimal stimulation regimen. The method may further comprise cyclically conveying stimulation energy between the different pairs of electrodes one-at-a-time to stimulate at least one muscle of a urethral sphincter muscle of the female patient without substantially stimulating pelvic floor muscles of the female patient.

In one embodiment, the method further comprises mechanically fitting the transvaginal stimulation device to the female patient. If the probe body comprises telescoping proximal and distal probe bodies, mechanically fitting the transvaginal stimulation to the female patient may comprise axially displacing the telescoping probe bodies relative to each other to vary a distance between the pair of electrodes and the waist of the probe body. Mechanically fitting the transvaginal stimulation device to the female patient may comprise axially displacing the pair of electrodes relative to the probe body to vary a distance between the pair of electrodes and the waist of the probe body. Mechanically fitting the transvaginal stimulation device to the female patient may comprise inserting a plurality of different intravaginal stimulation devices having different distances between a pair of electrodes into the vaginal cavity of the female patient, and selecting the intravaginal stimulation devices from the plurality of different intravaginal stimulation devices.

Optionally, the method may further comprise wirelessly controlling operation of the transvaginal stimulation device via a patient control device. Another optional method further comprises terminating the stimulation energy conveyed between the electrodes by actuating a user interface disposed on the probe body. Another optional method further comprises extracting the probe body from the vaginal cavity of the female patient by grasping an extraction element extending proximally from the probe body. If the extraction mechanism comprises a fingerhold, the method may optionally further comprise approximating the pubic bone of the female patient when the probe body is fully disposed in the vaginal cavity of the female patient.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of preferred embodiments of the disclosed inventions, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects of the disclosed inventions are obtained, a more particular description of the disclosed inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

DETAILED DESCRIPTION OF THE ILLUSTRATED EMBODIMENTS

In contrast to the conventional approaches that treat stress urinary incontinence (SUI) in a female patient, particularly those that stimulate the pelvic floor muscles (e.g., the levator ani), the inventors have discovered that specifically stimulating the urethral sphincter muscle of the female patient will cause a greater contraction of the urethral sphincter muscle, and therefore, result in a relatively higher urethral closing pressure. Because the urethral sphincter muscle extends along 4/5ths the length of the urethra, and is surrounded by other muscles, including the pubococcygeal and puborectal portions of the pelvic floor muscles, specifically stimulating the urethral sphincter muscle while avoiding stimulation of other muscles in a female patient, especially during physical activity of the patient, presents unique challenges. The SUI treatment system described herein consistently and robustly stimulates the urethral sphincter muscle of a physically active female patient suffering from SUI. Although the SUI treatment system described herein lends itself well to the treatment of SUI in human female patients, it should be appreciated that the SUI treatment system described herein can be adapted to treat nonhuman female patients, e.g., older pets.

Figure 1A:
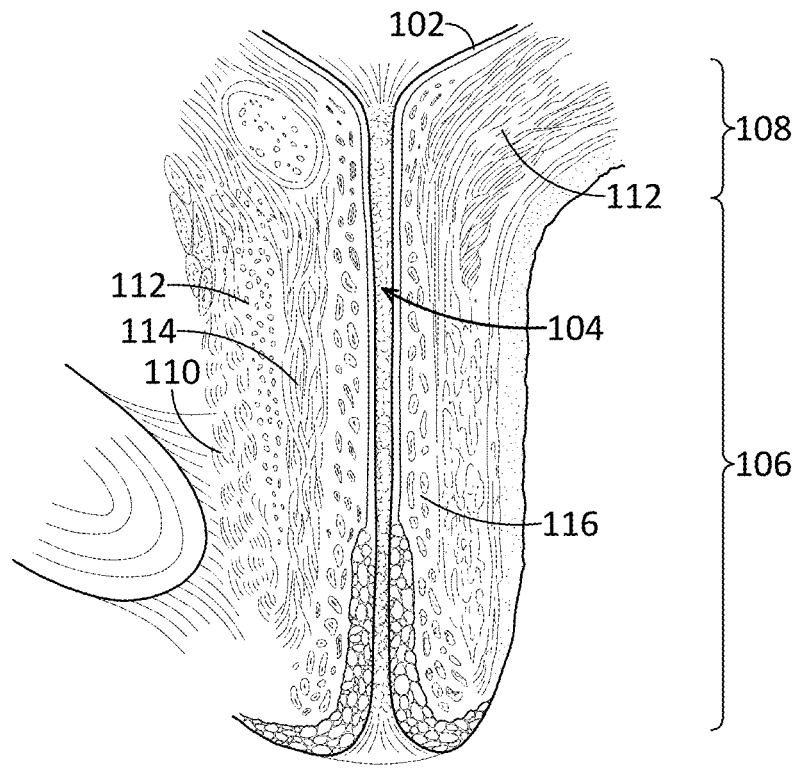
FIGS. 1A and 1B are anatomical views illustrating the periurethral structural components of a female.
Figure 1B:
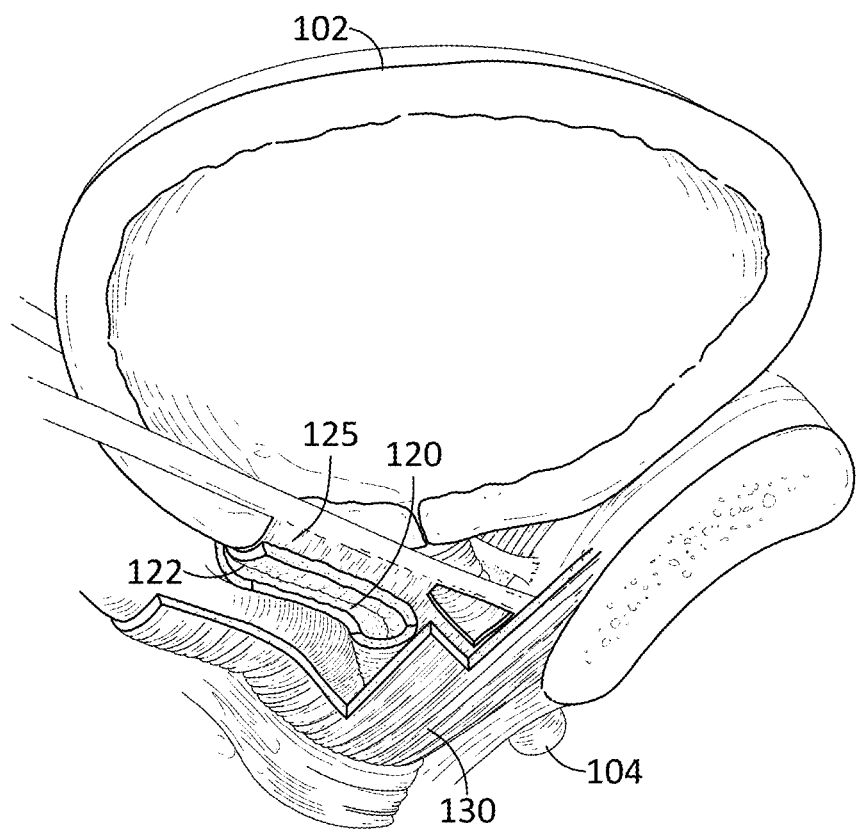

As shown in FIG. 1A, the periurethral components of a female patient 100 comprise a detrusor smooth muscle at the neck of the bladder 102 and the urethra 104, itself. The urethra 104 is approximately 4-5 cm long in a female, and is embedded in the connective tissue 125 supporting the anterior wall 122 of the vagina 120, as shown in FIG. 1B. The urethra 104 comprises a urethral sphincter 106, which extends lengthwise along the caudal 4/5ths of the urethra 102 to actively control the flow of urine from the bladder 102, and a nozzle 108, which extends lengthwise along the remaining cranial ⅕th of the urethra 102 to passively control the flow of urine from the bladder 102. The urethral sphincter 106 comprises three layers of muscle (an outer circumferential layer of striated muscle 110, a middle circumferential layer of smooth muscle 112, and an inner longitudinal layer of smooth muscle 114) and a vascular plexus 116 surrounding the urethral lumen 118 (see James A. Ashton-Miller and John O. L. DeLancey, "Functional Anatomy of the Female Pelvic Floor, Ann. N.Y. Acad Sci. 1101:266-296 (2007)). The circumferential striated muscle 110 is under voluntary control, while the circumferential smooth muscle 112 and longitudinal smooth muscle 114 are under involuntary or autonomic control. It is only the circumferential striated muscle 110 that contributes to the voluntary and reflex closure of the urethra 104 during acute instances that result in increased abdominal pressure (e.g., coughing, sneezing, laughing, etc.).

The current dogma is that all of the periurethral structural components listed above, including the circumferential striated muscle 110, the circumferential smooth muscle 112, the longitudinal smooth muscle 114, and the vascular plexus 116, contribute equally to urethral closure pressure, and thus, are the primary structures preventing the involuntary release of urine from the bladder 102. As such, all of these periurethral structural components contribute to urinary continence, and when dysfunctional, cause urinary incontinence. Based on this dogma, conventional wisdom dictates that electrical stimulation be conveyed along the entire length of the urethra 104 to ensure that all of the periurethral structural components are trained or reeducated, thereby providing maximum efficacy for the treatment of SUI in a female patient.

However, in contrast to this, the inventors have discovered that delivering focused stimulation to the middle region of the urethra 104 containing the circumferential striated muscle 110 achieves comparatively higher urethral closure pressure, and thus, is more desirable than stimulating all of the periurethral structural components along the entire length of the urethra 104 in the patient 100. The inventors have designed and tested an SUI treatment system 10 that specifically stimulates the circumferential striated muscle 110 (i.e., the mid-urethral striated sphincter muscle) of the female patient 100 in a consistent and robust manner even during physical activity of the female patient 100.

Figure 2:
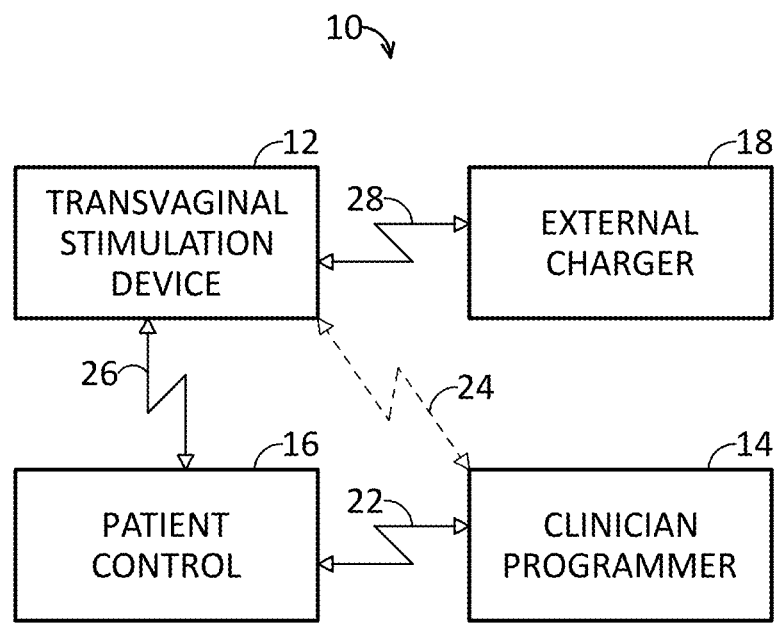
FIG. 2 is a block diagram of a stress urinary incontinence (SUI) treatment system constructed in accordance with one embodiment of the disclosed inventions.

Referring now to FIG. 2, one embodiment of the SUI treatment system 10 generally comprises a transvaginal stimulation device 12, a clinician programmer 14, a patient controller 16, and an external charger 18.

Figure 3A:
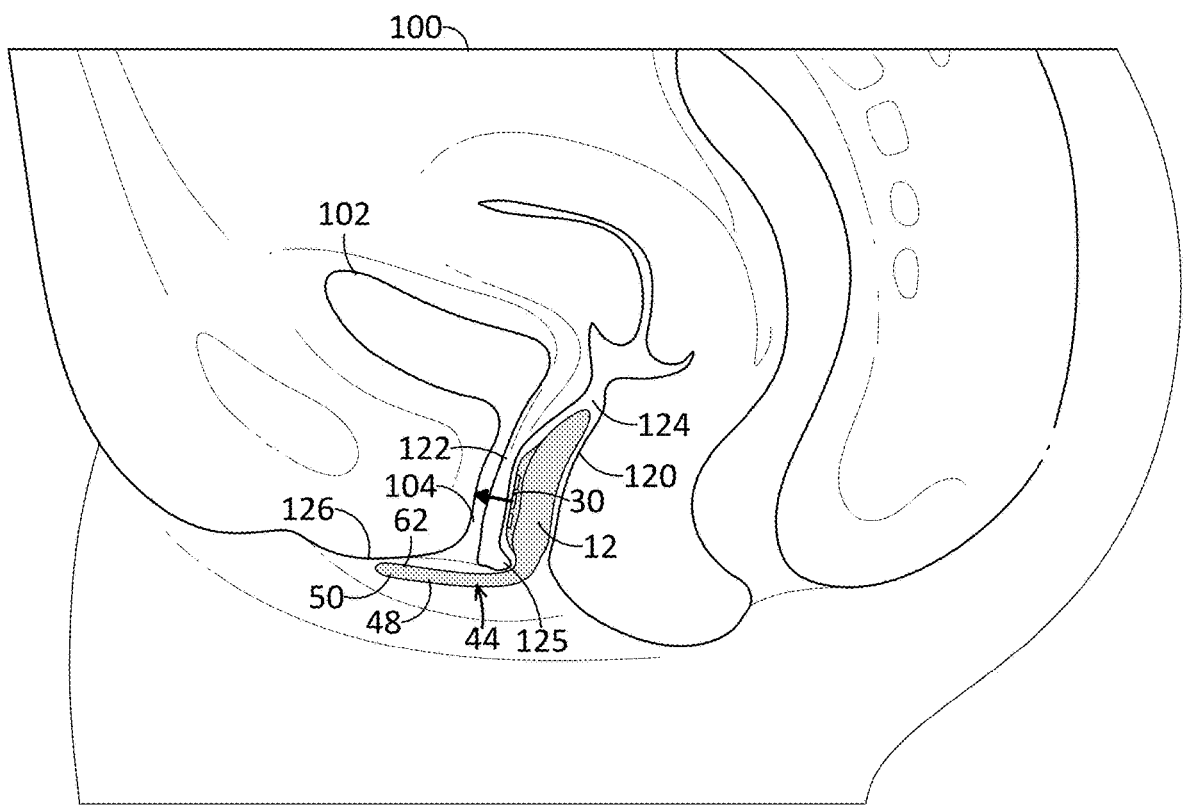
FIGS. 3A-3C are anatomical views illustrating the transvaginal stimulation device of FIGS. 6A-6F inserted into the vaginal cavity of a female patient.
Figure 3B:
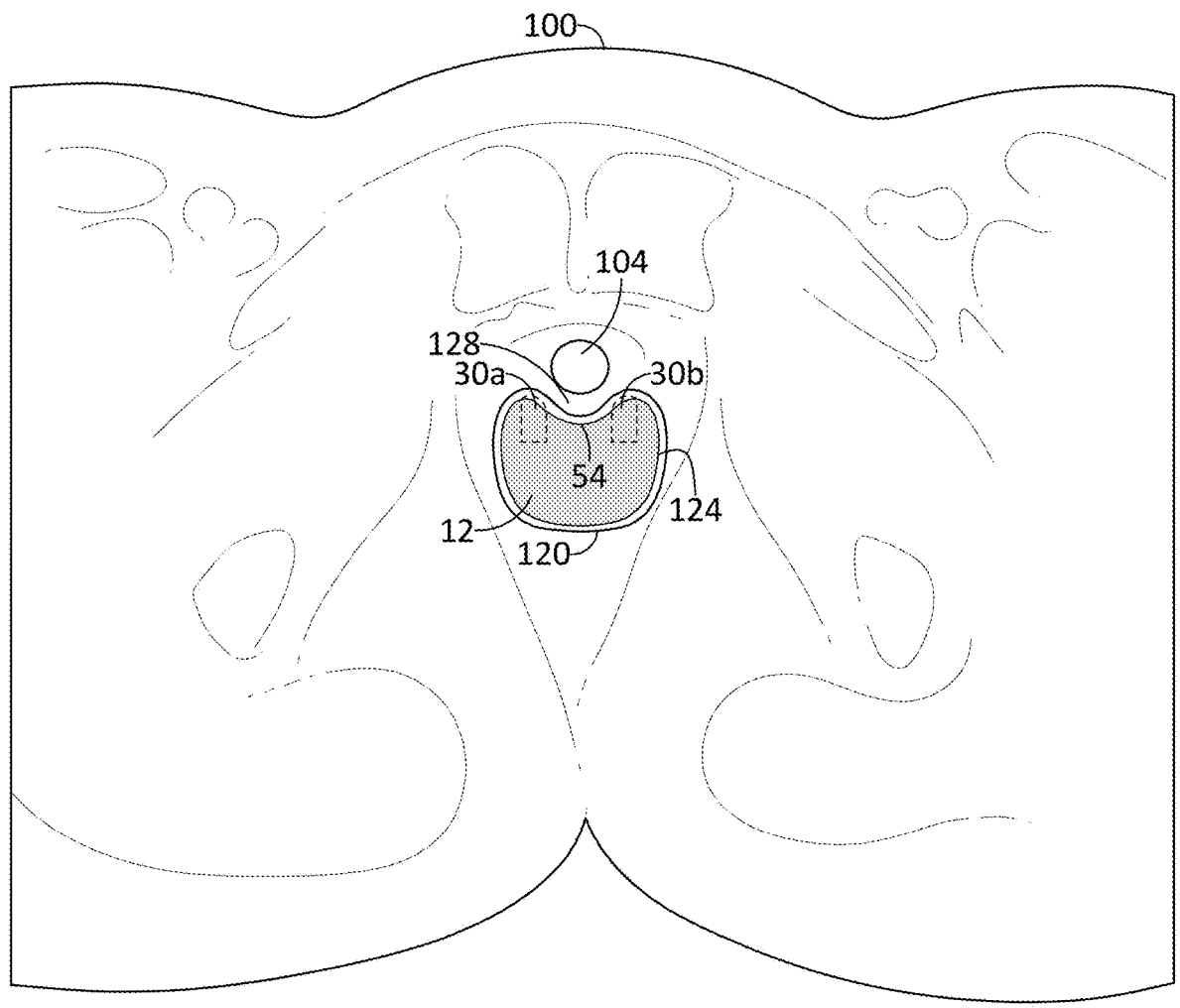
Figure 3C:
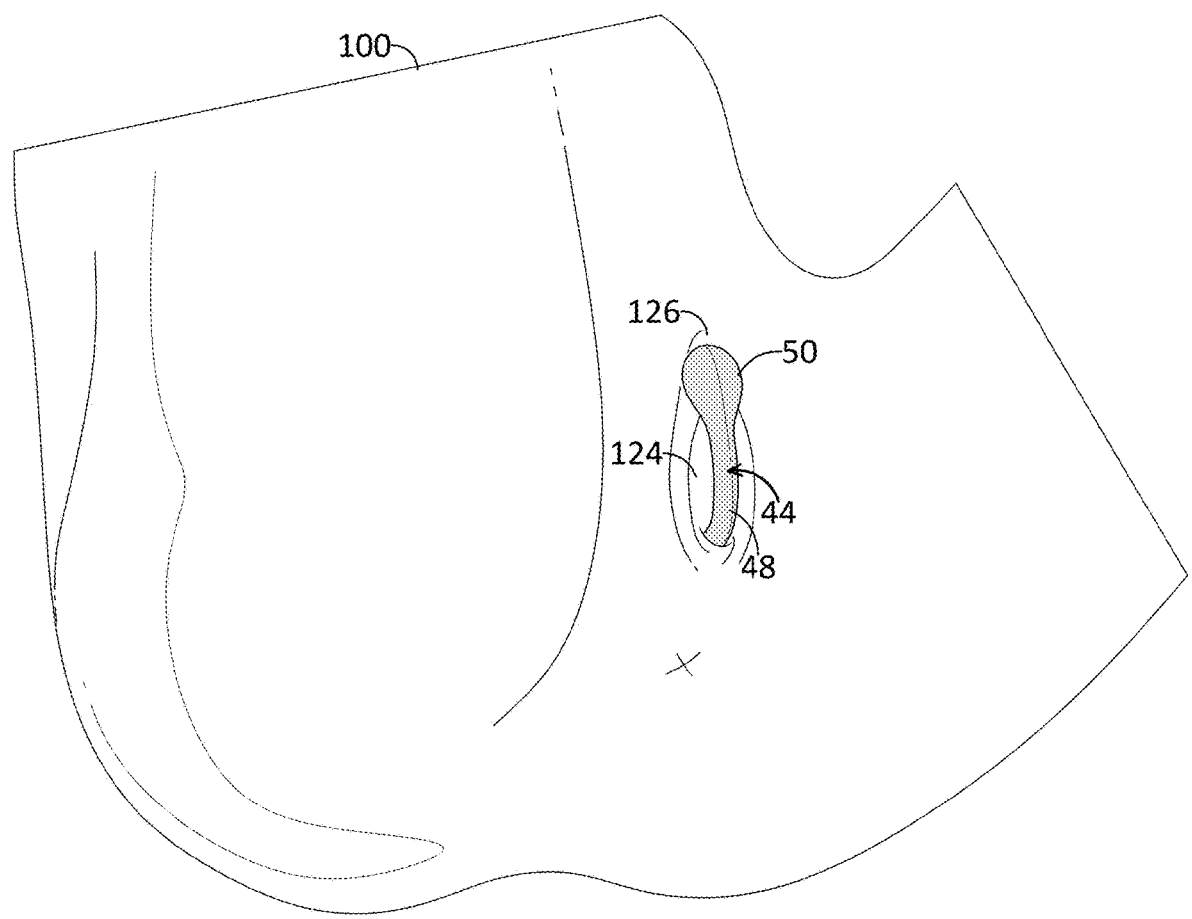

As shown in FIGS. 3A-3C, the transvaginal stimulation device 12 is configured for being introduced into a vaginal cavity 124 of the patient 100, and for delivering electrical stimulation energy (shown by arrow) only through the anterior wall 122 of the vagina 120 towards the middle region of the urethra 104 to target the mid-urethral striated sphincter muscle 110 of the patient 100, which has been found to be at least as effective at increasing urethral closure pressure as stimulating the pelvic floor muscles surrounding the vagina 120, while stimulating far fewer muscles that are not responsible for urinary incontinence.

Once the transvaginal stimulation device 12 is inserted into the vaginal cavity 124 of the patient 100, the clinician programmer 14 can be used to program the transvaginal stimulation device 12 in a clinical setting. While it is contemplated that targeted stimulation of the mid-urethral striated sphincter muscle 110 of the patient 100 by the transvaginal stimulation device 12 will provide a robust means for treating the SUI of the patient 100, as will be described in further detail below, it may be desirable to perform a fitting session to fine tune or optimize such treatment. For example, different transvaginal stimulation regimens may be applied to the patient 100 by controlling the transvaginal stimulation device 12 via the clinician programmer 14 and, in response to each stimulation regimen, observing biofeedback in the form of a detected urethral closure pressure, which has been shown to be highly correlated to SUI. The stimulation regimen or regimens that result in maximum urethral closure pressure can then be selected. Different stimulation frequencies are known to be required to recruit striated muscle (i.e., 50 Hz) than are required to recruit smooth muscle (13 Hz). The difference in response of the two types of muscle to electrical stimulation of the appropriate frequency can be determined by the time constant of the change in closure pressure, with striated muscle reaching a maximum tetanic contraction in about a fifth of a second, while smooth muscle may take many seconds to reach a maximum contraction.

Figure 4:
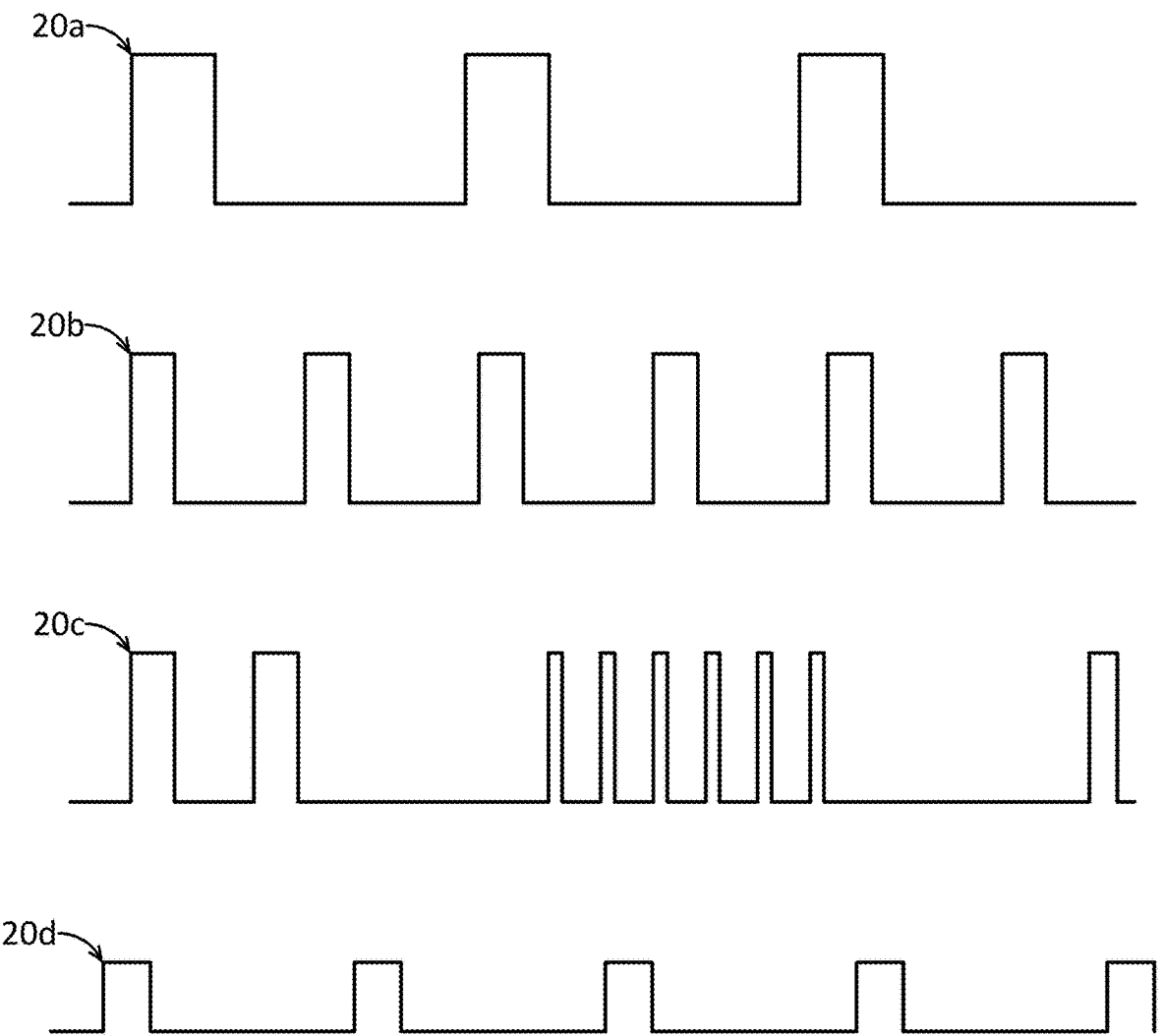
FIG. 4 are timing diagrams illustrating various exemplary electrical pulse trains that can be generated by the transvaginal stimulation device of FIG. 2.

Using the biofeedback as guidance, the clinician can operate the clinician programmer 14 to generate custom stimulation programs (each comprising clinician detailed stimulation parameters) and programming the transvaginal stimulation device 12 with the stimulation programs. For example, four exemplary stimulation programs (e.g., warm-up, endurance, massage, cool down) corresponding to four different electrical pulse trains 20a-20d are illustrated in FIG. 4. The transvaginal stimulation device 12 may be programmed to sequentially step through the different stimulation programs in accordance with a timing protocol, or any one of the stimulation programs may be actuated via the patient controller 16, as discussed below.

In the illustrated embodiment, the clinician programmer 14 takes the form of a laptop computer, although in alternative embodiments, the clinician programmer 14 may take the form of a conventional Smartphone configured with a smartphone application with programming capabilities. The clinician programmer 14 may perform this function by indirectly communicating with the transvaginal stimulation device 12, through the patient controller 16, via a bi-directional wireless communications link (e.g., using a short-range infrared (IR) protocol) 22. Alternatively, the clinician programmer 14 may directly communicate with the transvaginal stimulation device 12 via the bi-directional wireless communications link 24 (e.g., using a short-range radio-frequency (RF) protocol, such as a Bluetooth protocol, although other types of short-range RF protocols, such as a Wi-Fi protocol, can be used). More alternatively, the clinician programmer 14 may communicate with the transvaginal stimulation device 12 via a wired connection. The clinician detailed modulation parameters provided by the clinician programmer 14 may also be used to program the patient controller 16, so that the stimulation parameters can be subsequently modified by operation of the patient controller 16 in a stand-alone mode (i.e., without the assistance of the clinician programmer 14).

The patient controller 16 may be used to telemetrically control the transvaginal stimulation device 12 via a bi-directional wireless communications link 26 (e.g., using a short-range RF protocols, such as a Bluetooth protocol, although other types of short-range RF protocols, such as a Wi-Fi protocol, can be used). Alternatively, the patient controller 16 may communicate with the transvaginal stimulation device 12 via a wired connection. In any event, control by the patient controller 16 allows the transvaginal stimulation device 12 to be turned on or off, select one of a plurality of different stimulation programs (corresponding to different electrical pulse trains) previously programmed into the transvaginal stimulation device 12 via the clinician programmer 14, and to modify other parameters of the electrical stimulation energy (e.g., to adjust the intensity of the electrical stimulation or cause the transvaginal stimulation device 12 to ramp up or ramp down the electrical stimulation). The patient controller 16 can take the form of, e.g., a Smartphone. The patient controller 16 may optionally track patient compliance, send reminders and/or encouragement to the patient, share data with physicians, display remaining time left during a session, and track the patient progress.

The external charger 18 is a portable device used to transcutaneously charge the transvaginal stimulation device 12 via an inductive link 28. The external charger 18 may, e.g., wirelessly charge the transvaginal stimulation device 12 or may use contacts to charge the transvaginal stimulation device 12. In the latter case, the external charger 18 may take the form of a storage container that completely encloses the transvaginal stimulation device 12 during the charging process. Alternatively, the transvaginal stimulation device 12 may be recharged by plugging the transvaginal stimulation device 12 into a household alternating current (AC) socket. More alternatively, the transvaginal stimulation device 12 may not be recharged at all, but instead contains a replaceable non-rechargeable battery. Once the transvaginal stimulation device 12 has been programmed by the clinician programmer 14, turned on by the patient controller 16, and charged by the external charger 18, the stimulation programs are run locally on the transvaginal stimulation device 12 during a stimulation session, and may thus function as programmed without the patient controller 16, clinician programmer 14, and external charger 18 being present. The stimulation sessions may be logged locally on the transvaginal stimulation device 12 and uploaded to the patient controller 16 or clinician programmer 14 when communication has been established over the bi-directional wireless link(s).

Figure 5:
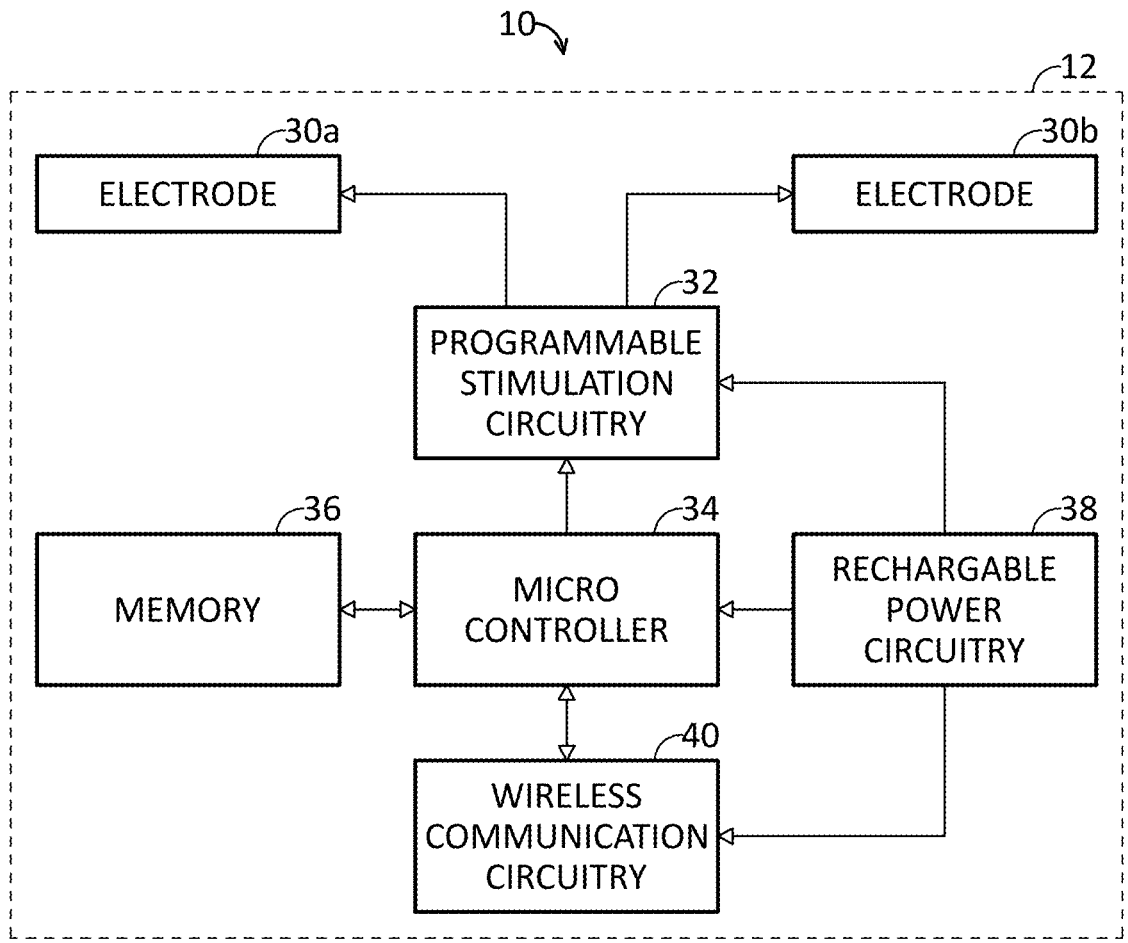
FIG. 5 is a block diagram of transvaginal stimulation device used in the SUI treatment system of FIG. 2.

Referring now to FIG. 5, the electrical components of the transvaginal stimulation device 12 will be described. The transvaginal stimulation device 12 generally comprises at least one pair of electrodes 30a, 30b (only one pair of electrodes illustrated in FIG. 5), programmable stimulation circuitry 32, a microcontroller 34, memory 36, a rechargeable power circuitry 38, and wireless communication circuitry 40.

In the preferred embodiment, the electrodes 30a, 30b are respectively activated as an anode and a cathode, such that electrical stimulation energy is transmitted between the electrodes 30a, 30b in a bipolar manner. Although the electrical stimulation energy may be delivered as monophasic electrical energy (i.e., the pulses are either negative (cathodic) or positive (anodic), it is preferred that the electrical stimulation energy is delivered as multi-phasic electrical energy (e.g., a series of biphasic pulses, with each biphasic pulse including a negative (cathodic) pulse (during a first phase) and a positive (anodic) pulse (during a second phase) to prevent direct current charge transfer through tissue, thereby avoiding electrode degradation and cell trauma.

The programmable stimulation circuitry 32 is configured for generating electrical stimulation energy in accordance with a defined pulsed waveform having a specified pulse amplitude, pulse rate, pulse width, and pulse shape. In the preferred embodiment, the stimulation circuitry 32 comprises an integrated analog-to-digital converter (ADC) that constantly measures and adjusts the output voltage to maintain a constant current output, thereby guaranteeing constant output to the electrodes 30a, 30b during and between stimulation sessions.

In addition to controlling the operation of the transvaginal stimulation device 12, the microcontroller 34 programs the stimulation circuitry 32 in accordance with one or more stimulation programs stored in the memory 36. Each of the stimulation programs stored in memory may comprises a set of stimulation parameters (e.g., pulse amplitude (e.g., in the range of 30-40 mA), pulse rate (e.g., in the range of 20 Hz-60 Hz), pulse width (e.g., in the range of 0.1 ms-0.3 ms, and pulse shape) of the electrical stimulation energy (i.e., the pulse train) output by the stimulation circuitry 32. In one embodiment, up to four stimulation programs may be stored in the memory, although in other embodiments, more or less than four stimulation programs may be stored in the memory. The memory may also store a timing protocol in the case where the transvaginal stimulation device 12 is programmed to automatically step through the different stimulation programs, as well as log stimulation sessions performed by the transvaginal stimulation device 12.

The rechargeable power circuitry 38 comprises a battery, e.g., lithium-ion or lithium-ion polymer battery, and regulation circuitry (not shown). The battery outputs unregulated voltage to the regulation circuitry, which outputs regulated power to the stimulation circuitry 32, as well as the other components, of the transvaginal stimulation device 12. The power circuitry 38 is recharged using rectified AC power (or DC power converted from AC power) via the power circuitry 38, which comprises an AC coil (not shown). To recharge the power circuitry 38 while the transvaginal stimulation device 14 is disposed in the vaginal cavity 124 of the patient 100, the transvaginal stimulation device 14 may be placed within the external charger 18, which generates an AC magnetic field, or alternatively, the external charger 18 is placed against, or otherwise adjacent, to the patient 100 over the transvaginal stimulation device 14. The AC magnetic field emitted by the external charger 18 induces AC currents in the AC coil of the rechargeable power circuitry 38 over the inductive link 28 (shown in FIG. 2), which rectifies the AC current to produce DC current, which is used to charge the power circuitry 38. Alternatively, the transvaginal stimulation device 14 may be recharged in a storage container or external charger while not in use.

The communication circuitry 40 comprises an antenna (not shown) for receiving programming data (e.g., stimulation programs) from the clinician programmer 14 over the wireless communications link 26 (shown in FIG. 1), which programming data is stored in the memory, and patient control data (e.g., on/off, amplitude control, stimulation program selection) from the patient programmer 14 over the wireless communications link 26. The communication circuitry 40 may also transmit status information or logged stimulation sessions to the clinician programmer 14 or patient controller 16 over the communications link 26.

Referring to FIGS. 6A-6F, one embodiment of a transvaginal stimulation device 12 will now be described. Focused stimulation of the mid-urethral striated sphincter muscle 110 presents challenges in that the anatomy of the vaginal cavity 124 and location of the middle region of the urethra 104 relative to the vaginal cavity 124 may vary widely over patients. The transvaginal stimulation device 12 is aptly and robustly capable of treating a wide variety of patients while focusing stimulation energy on the mid-urethral striated sphincter muscle 110 of a patient 100.

The transvaginal stimulation device 12 generally comprises a probe body 42, an extraction mechanism 44 extending from a proximal region 43 of the probe body 42, an optional minimal user interface (UI) 46 located on the proximal region 43 of the probe body 42, and a pair of electrodes 30a, 30b disposed on the probe body 42. As will be described in further detail below, the transvaginal stimulation device 12 may optionally comprise additional pairs of electrodes.

The extraction mechanism 44 is designed to extend outside of the vaginal cavity 124 of the patient 100, thereby providing a convenient means of extracting the transvaginal stimulation device 12 from the vaginal cavity 124 of the patient 100, e.g., after a stimulation session has been completed. To this end, the extraction mechanism 44 comprises an elongated tail member 48 affixed to the proximal region 43 of the probe body 42, and a fingerhold 50 affixed to the elongated tail member 48. The elongated tail member 48 has a pre-shaped C-geometry, such that the fingerhold 50 is disposed above the stimulating side 52a of the probe body 42 in the absence of force. While the transvaginal stimulation device 12 is fully disposed in the vaginal cavity 124 of the patient 100, a distal facing surface 62 of the fingerhold 50 (shown in FIG. 6F) approximates the pubic bone 126 of the patient 100, without placing undue pressure on the clitoris of the patient 100, causing the elongated tail member 48 to form an angle with the longitudinal axis of the probe body 42 of approximately 90 degrees, as illustrated in FIG. 3A. The fingerhold 50 of the extraction mechanism 44 also serves as a visual indicator to ensure that the electrodes 30a, 30b of the transvaginal stimulation device 12 are facing the anterior wall 122 of the vagina 120. That is, when the fingerhold 50 is in the 12 o'clock position, immediately under the pubic bone 126 of the patient 100, as illustrated in FIG. 3C, the patient 100 can visually confirm that the electrodes 30a, 30b of the transvaginal stimulation device 12 are facing the anterior wall 122 of the vagina 120, and furthermore, that the probe body 42 is not cock-eyed (i.e., the distal tip of the probe body 42 does not veer left, right, or up). In contrast, if the fingerhold 50 is not in the 12 o'clock position, the patient 100 knows that the transvaginal stimulation device 12 must be adjusted to face the electrodes 30a, 30b towards the anterior wall 122 of the vagina 120.

Figure 7:
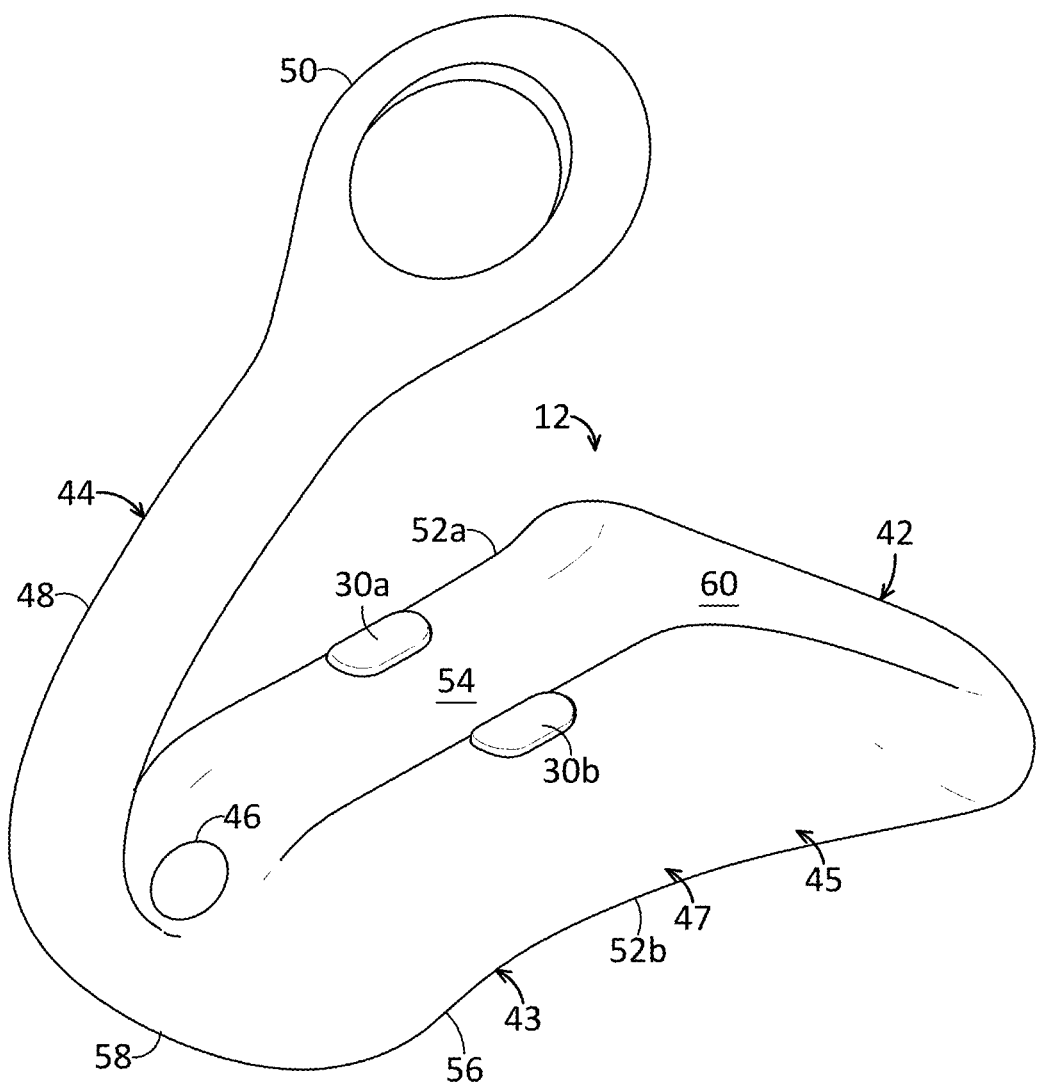
FIG. 7 is an external view of another embodiment of a transvaginal stimulation device for use in the SUI treatment system of FIG. 2.

In an optional embodiment illustrated in FIG. 7, the fingerhold 50 is shaped as a loop that may house a radio frequency (RF) antenna to facilitate bi-directional communication between the transvaginal stimulation device 12 and the clinician programmer 14 and patient controller 16 (shown in FIG. 2), as described above.

Figure 6A:
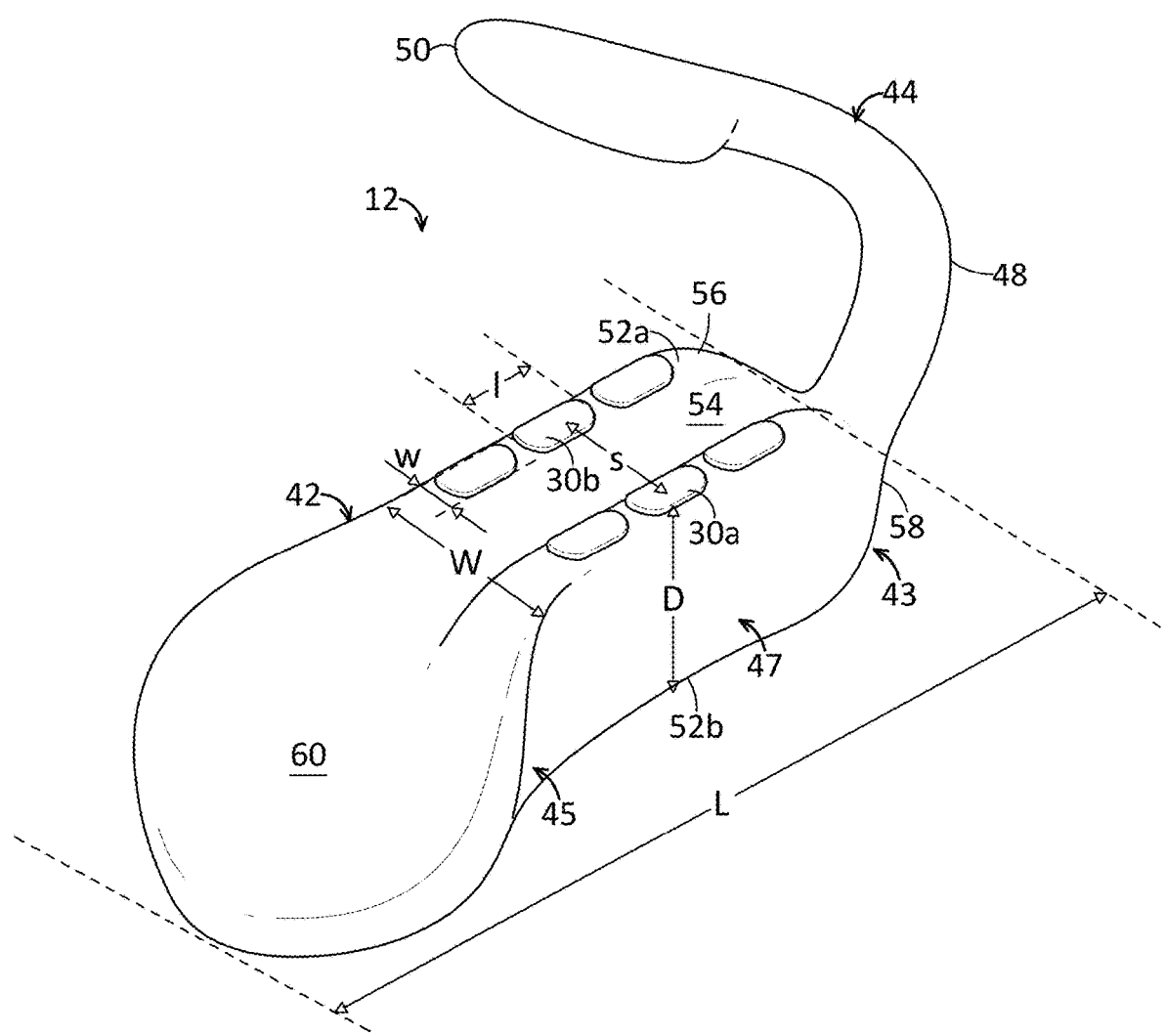
FIGS. 6A-6F are various external views of one embodiment of a transvaginal stimulation device for use in the SUI treatment system of FIG. 2.
Figure 6B:
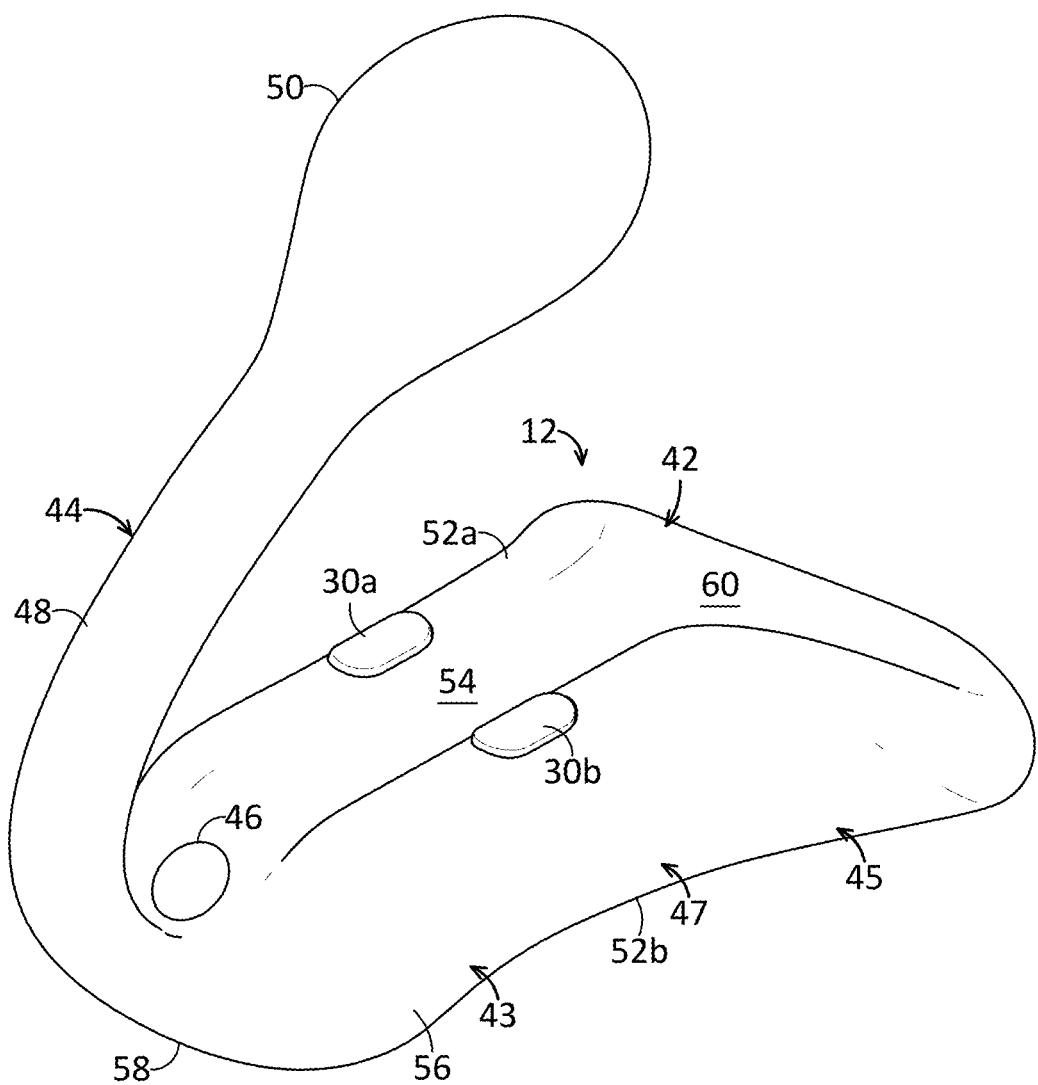
Figure 6C:
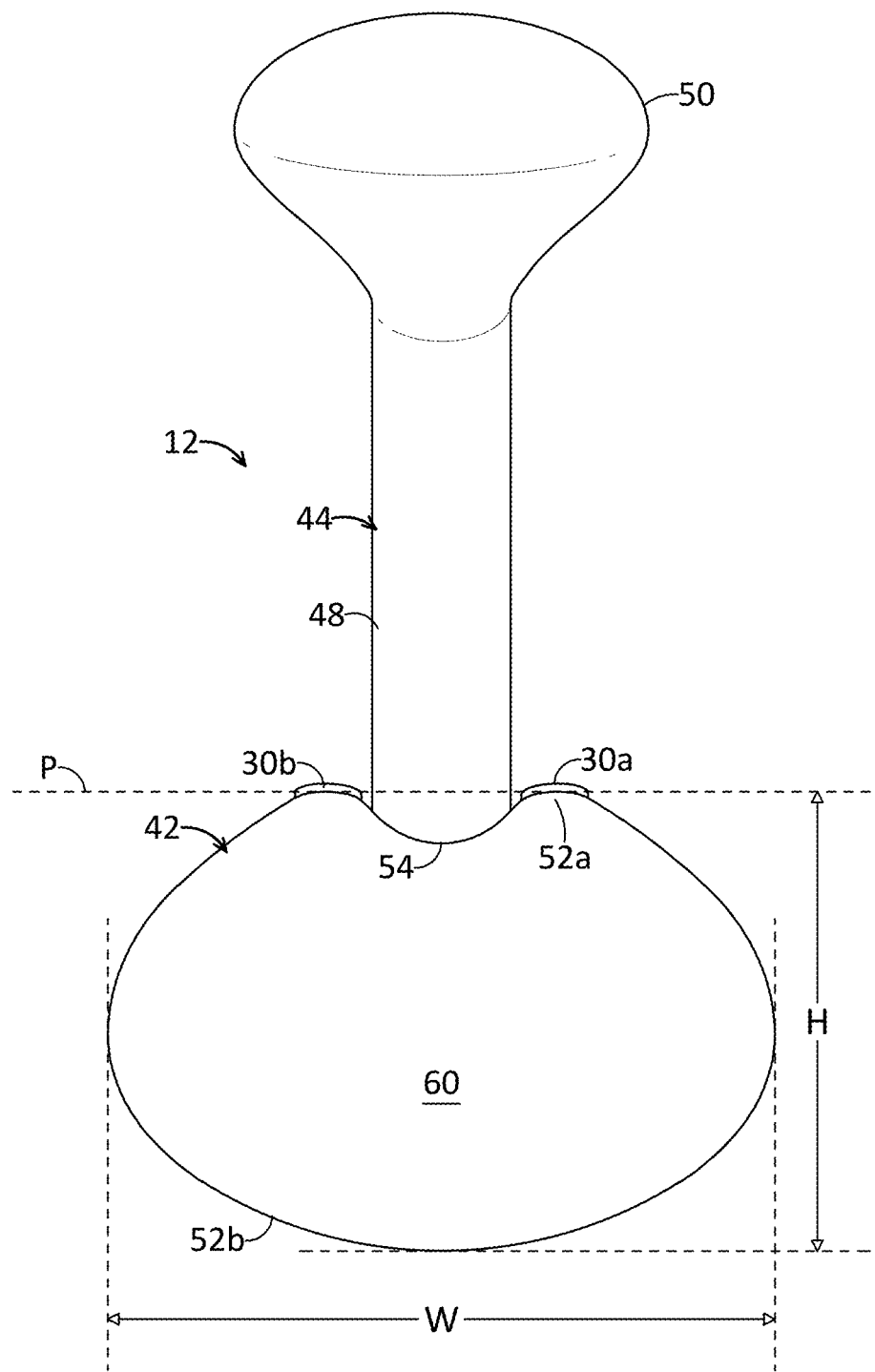
Figure 6D:
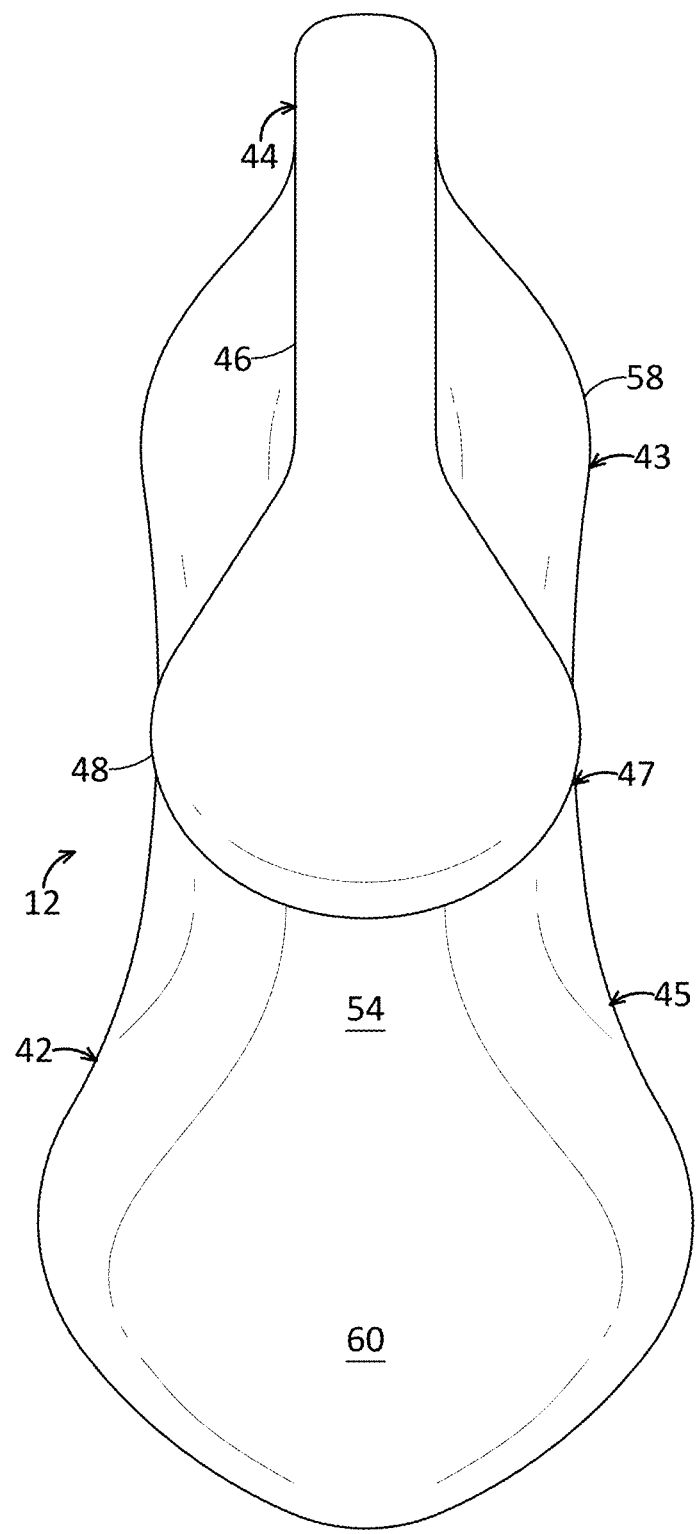
Figure 6E:
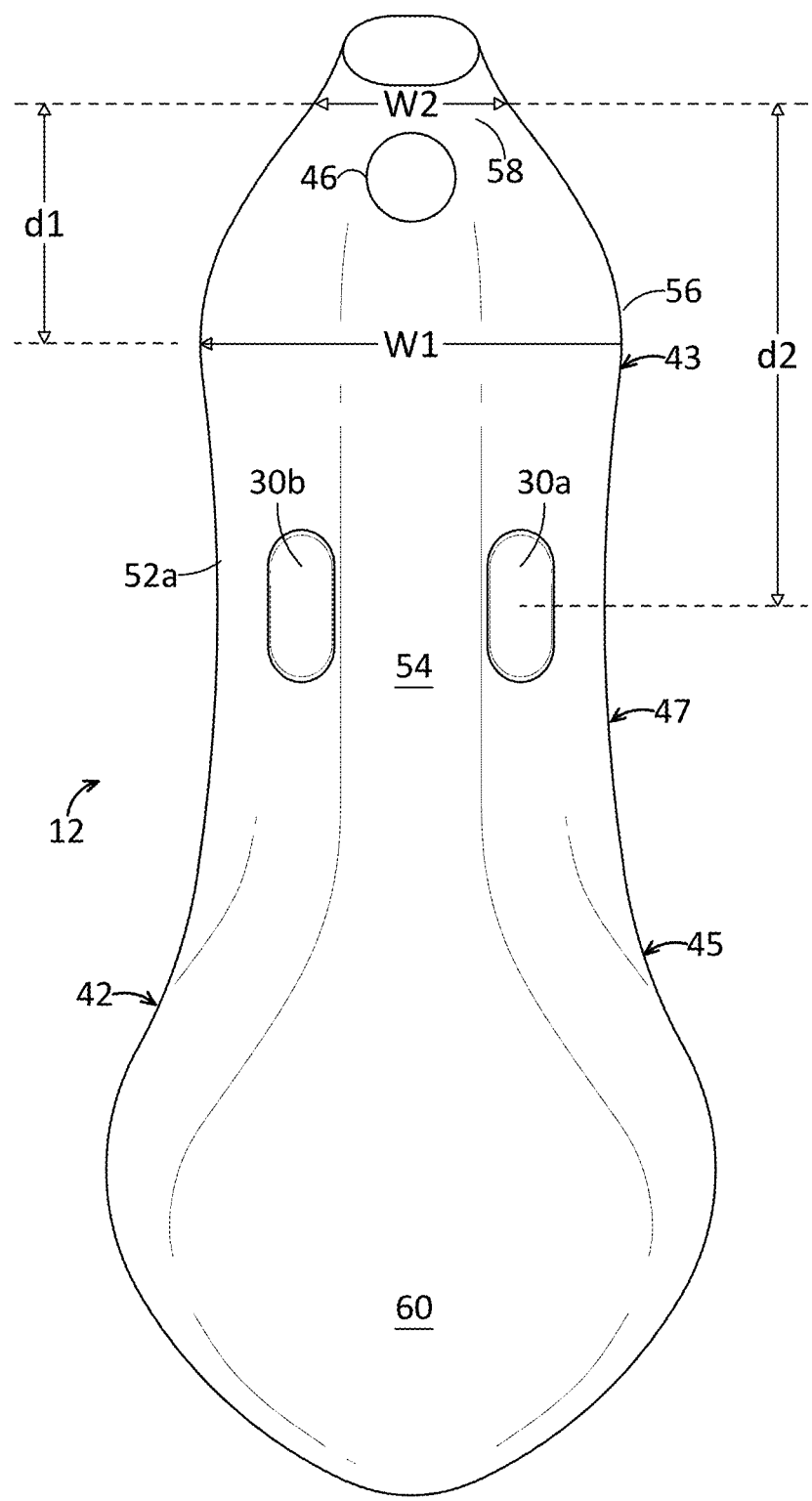

As shown in FIGS. 6B and 6E, the minimal UI 46 can be actuated by the patient 100 to wake up the transvaginal stimulation device 12 and to communicate the state of the transvaginal stimulation device 12 to the patient 100. The minimal UI 46 may also be actuated to turn on the transvaginal stimulation device 12 (i.e., activate the stimulation circuitry) or turn off the transvaginal stimulation device 12 (i.e., deactivate the stimulation circuitry) to provide the patient 100 an alternative means of initiating or ceasing a stimulation session, e.g., if the patient controller 16 is lost or otherwise out of reach of the patient 100.

The probe body 42 may be semi-rigid or rigid and can be composed of both rigid and flexible sections. The rigid sections of the probe body 42 may be composed of a rigid biocompatible plastic, e.g., acrylonitrile butadiene styrene (ABS), polycarbonate, polypropylene, or other similar plastics, and the flexible sections of the probe body 42 may be composed of a biocompatible elastomer, e.g., silicone, polyurethane, nitrile rubber, or other similar materials. The probe body 42 is sized and shaped to be fully inserted into the vaginal cavity 124 of the patient 100, and may, e.g., take the form of a casing that hermetically contains the internal electrical components described above with respect to FIG. 5. Although it is preferred that the stimulation circuitry 32 be contained with the probe body 42, in alternative embodiments, the stimulation circuitry 32 may reside outside of the probe body 42, in which case, it can be electrically coupled to the electrodes 30a, 30b via an electrical cord (not shown).

The probe body 42 has a stimulating side 52a on which the pair of electrodes 30a, 30b is disposed, and a diametrically opposing non-stimulating side 52b completely free of electrodes, such that electrical stimulation energy can only be emitted unidirectionally from the stimulating side 52a of the probe body 42. In the context of the transvaginal stimulation of the mid-urethral striated sphincter muscle 110

(shown in FIG. 1A), the stimulating side 52a can be considered the anterior face of the probe body 42, whereas the non-stimulating side 52b can be considered the posterior face of the probe body 42. As shown in FIG. 6A, the probe body 42 has a length L extending in the longitudinal direction, a width W extending in the lateral direction, and a depth D extending perpendicularly to the length L and width W.

Significantly, the stimulating side 52a of the probe body 42 has a transversely scalloped or concave region 54 between and extending at least the length l of the electrodes 30a, 30b. As can be best appreciated in FIG. 3B, this concave region 54 of the stimulating side 52a facilitates location of the urethra 104 in the middle of the transvaginal stimulation device 12 equidistant between the electrodes 30a, 30b. The concave region 54 of the stimulating side 52a conforms to the natural convex surface of the anterior wall 122 of the vagina 120 caused by the urethral carina 128 (shown in FIG. 3B), thereby minimizing stretching of the tissue of the anterior wall 122, which may otherwise occur if the stimulating side 52a had a transversely flat or convex contour. The concave region 54 also facilitates low resistance contact of the electrodes 30a, 30b with vaginal tissue and disposes the electrodes 30a, 30b as close to the urethra 104 as is possible in a transvaginal approach thereby providing spatial specificity. The concave region 54 may have a radius of curvature of, e.g., 1 cm (see FIG. 6C), and a length commensurate with the length L of the probe body 42 (see FIG. 6A), such that the entire length of the urethral carina 128 will be located equidistantly between the electrodes 30a, 30b.

Much of the probe body 42 is uniquely shaped with an elliptical cross-section in the transverse plane (see FIG. 6C) in order to maintain its position (both longitudinally and rotationally) within the vaginal cavity 124 of the patient 100, thereby ensuring that the electrical stimulation energy continues to be directed towards and focused on the mid-urethral striated sphincter muscle 110 of the patient 100, even when the patient 100 is performing physical activity.

To this end, the length L of the probe body 42 is commensurate with the length of the vaginal cavity 124 (e.g., in the range of 4 cm-8 cm). The length L of the probe body 42 will generally be greater than the width W of the probe body 42 to mimic the vaginal cavity 124 of the patient 100. Notably, the vaginal cavity 124 has a non-circular cross-section, and in particular, is flat and wide, with the anterior and posterior walls of the vagina 120 contacting each other. As can be seen in FIG. 6C, the cross-sectional elliptical shape of the probe body 42 reflects the natural shape of the middle and cranial regions of the vaginal cavity 124. Because the cross-section of the natural vaginal cavity 124 is non-circular, and in particular, has an elliptical cross-section, the probe body 42 likewise has a non-circular (in this case, an elliptical) cross-section, with the greatest lateral extent of its width W being greater than its depth D to mimic the vaginal cavity 124. It can be appreciated that the probe body 42 mimics the non-circular cross-section of the vaginal cavity 124, thereby resisting rotation of the transvaginal stimulation device 12 relative to the vaginal cavity 124. In contrast, a cylindrical probe body having a circular cross-section would provide little to no resistance to rotation of the transvaginal stimulation device 12 within the vaginal cavity 124.

The cross-section in the transverse plane (both width W and depth D) of the probe body 42 along its length L is also uniquely shaped to ensure that the transvaginal stimulation device 12 is properly seated axially within the vaginal cavity 124 of the patient 100 in a stable and repeatable manner. In this manner, the electrodes 30a, 30b will be axially aligned with the mid-urethral striated sphincter muscle 110 of the patient 100 in a consistent manner once the transvaginal stimulation device 12 is inserted in the vaginal cavity 124 of the patient 100.

To this end, the width W at the proximal region 43 of the probe body 42 laterally flares outward in the proximal direction to form shoulders 56, and then laterally tapers inward in the proximal direction to its narrowest point to form a waist 58, as best shown in FIG. 6E. In the embodiment illustrated in FIG. 6E, the width W2 of the waist 58 of the probe body 42 is less than half of the width W1 of the shoulders 56 of the probe body 42, and preferably less than one-third of the width W1 of the shoulders 56 of the probe body 42. For example, the width W2 of the waist 58 may be in the range of 1 cm-1.5 cm. The axial distance d1 between the shoulders 56 of the probe body 42 and the waist 58 of the probe body 42 is preferably in the range of 1.0 cm to 2.0 cm, and in the illustrated embodiment, is 1.5 cm.

Figure 6F:
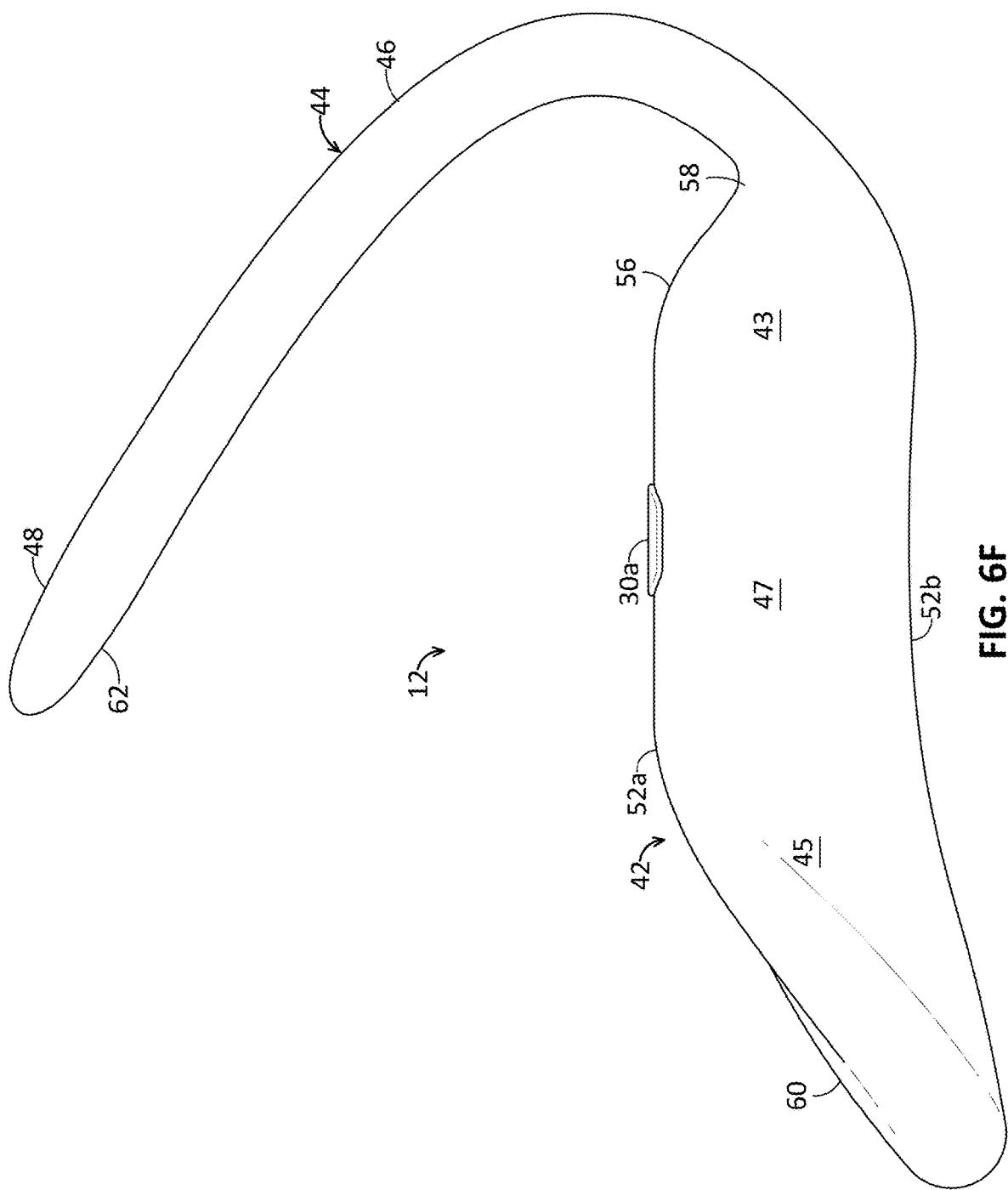

The inventors have also appreciated that the cranial end of the vaginal cavity 124 widens and angles posteriorly, and have taken advantage of this anatomical feature by shaping a distal region 45 of the probe body 42 to mimic the cranial end of the vaginal cavity 124. In particular, as illustrated in FIG. 6E, the width W at the distal region 45 of the probe body 42 laterally flares outward in the distal direction from a laterally narrow mid-region 47 to form the flattened scoop 60. As illustrated in FIG. 6F, the flattened scoop 60 is flattened, having a depth that is substantially less the depth of the mid-region 47 of the probe body 42, and angles downward away from the stimulating 52a of the probe body 42 to conform to the posteriorly angled cranial end of the vaginal cavity 124.

Figure 8A:
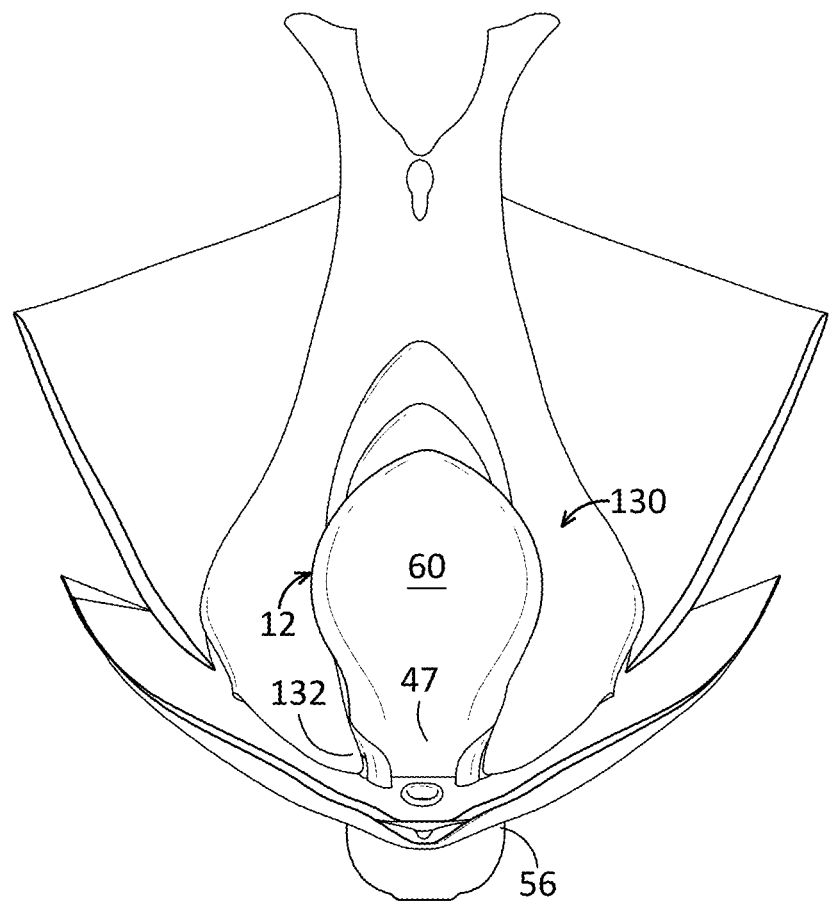
FIGS. 8A and 8B are anatomical views illustrating the transvaginal stimulation device of FIGS. 6A-6F being stabilized by the levator ani of a female patient.
Figure 8B:
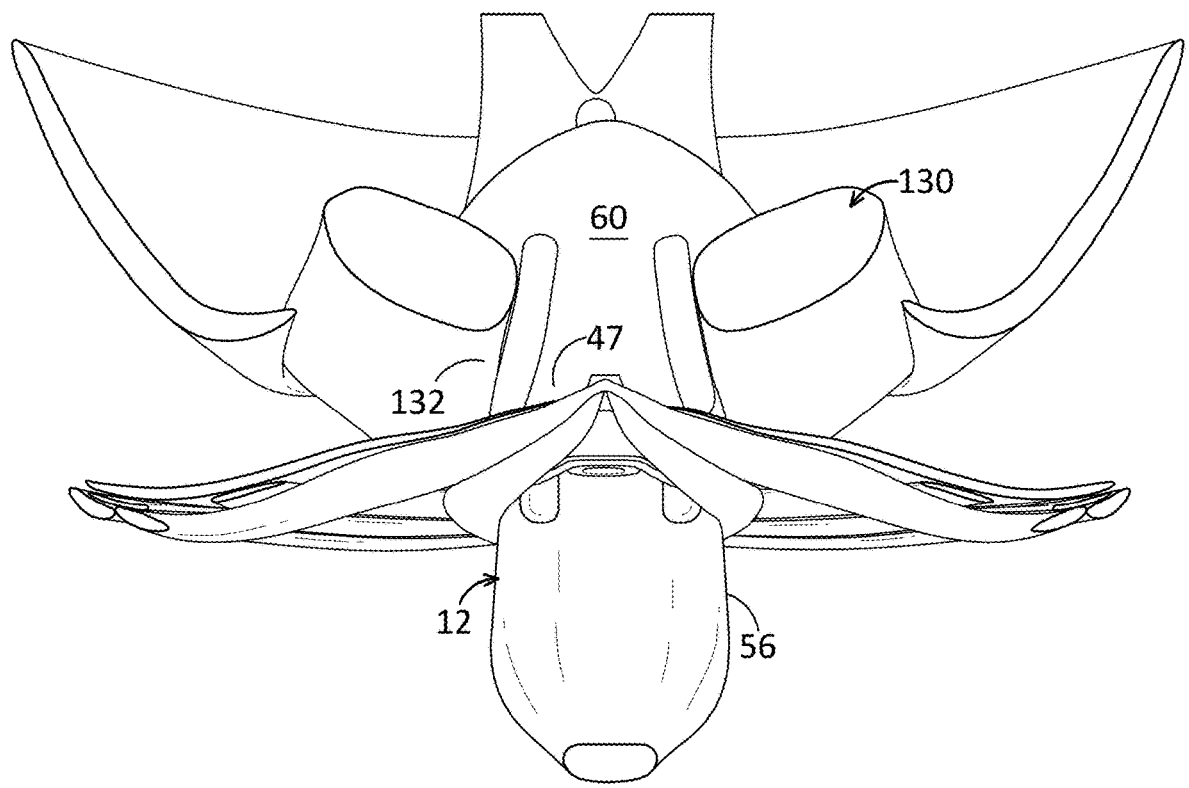

As illustrated in FIGS. 8A and 8B, when the probe body 42 is fully disposed within the vaginal cavity 124, the levator ani 130 exerts an inward medial compressive force on the laterally narrower mid-region 47 between the shoulders 56 and the flattened scoop 60, thereby securely seating and facilitating retention of the transvaginal stimulation device 12 longitudinally within the vaginal cavity 124. Thus, the probe body 42 is axially stabilized within the vaginal cavity 124, naturally helping to prevent it from being expelled by either gravity or intraabdominal pressure. Notably, the laterally narrow mid-region 47 of the probe body 42 conforms to where a region 132 of the levator ani 130 naturally indents the lateral margins of the vagina 120 inward when the probe body 42 is fully disposed in the vaginal cavity 124, thereby facilitating correct seating of the probe body 42 within the vaginal cavity 124, and location and retention of the electrodes 30a, 30b adjacent the mid-urethral striated sphincter muscle 120. Furthermore, because the flattened scoop 60 is flattened, as best illustrated in FIG. 6F, the flattened scoop 60 serves to further resist rotation of the transvaginal stimulation device 12 relative to the vaginal cavity 124.

Referring to FIG. 6A, the electrodes 30a, 30b have outer exposed, electrically conductive, tissue-contacting surfaces, such that the electrodes 30a, 30b may be placed into electrical contact with tissue, and in this case, the anterior wall 122 of the vagina 120 in which the transvaginal stimulation device 12 is inserted (shown in FIG. 3A). Significantly, as best shown in FIG. 6C, the tissue contacting surfaces of the electrodes 30a, 30b, which preferably have flattened faces, form an angle substantially equal to 180° (i.e., disposed on a plane P extending along the stimulating side 52a of the probe body 42), such that the electrodes 30a, 30b are placed into firm contact with in the anterior wall 122 of the vagina 120 when the transvaginal stimulation device 12 is inserted into the vaginal cavity 124. That is, as illustrated in FIG. 3B, because the anterior wall 122 of the vagina 120 is generally flat (as opposed to curved about a longitudinal axis of the probe body 42) in nature, contact between the electrodes 30a, 30b and the anterior wall 122 of the vagina 120 will be maximized if the electrodes 30a, 30b are disposed along the same plane (as opposed to being disposed circumferentially relative to each other as when disposed on a cylindrical probe body), and thus, focused stimulation of the mid-urethral striated sphincter muscle 110 will be made as efficient as possible. For the purposes of this specification, the tissue contacting surfaces of the electrodes 30a, 30b form an angle substantially equal to 180°, this angle being within a range of 160°-200°. Preferably, the tissue contacting surfaces of the electrodes 30a, 30b form an angle within the range of 170°-190°.

As shown in FIG. 6A, each of the electrodes 30a, 30b preferably is elongated, i.e., has a length l substantially greater than a width w. Notwithstanding this, each of the electrodes 30a, 30b preferably has a relatively short length l (e.g., in the range of 4 mm-12 mm), such that the stimulation energy is focused in the region adjacent the mid-urethral striated sphincter muscle 110. The electrodes 30a, 30b have an edge-to-edge lateral spacing s, which should not be so great that the current flowing between the electrodes 30a, 30b passes through the pelvic floor, but should not be so small that the current flows between the electrodes 30a, 30b without passing through the periurethral components of the patient 100. Notably, disposing the electrodes 30a, 30b on a plane along the stimulating side 52a of the probe body 42 facilitates minimization of the edge-to-edge lateral spacing s, which may otherwise be prohibitively increased if the electrodes 30a, 30b were radially disposed radially outward relative to the plane P. The edge-to-edge spacing s between the electrodes 30a, 30b is preferably in the range of 5 mm-25 mm, and more preferably in the range of 10 mm-20 mm, for optimal stimulation, although other ranges are contemplated by the invention.

Each of the electrodes 30a, 30b has a relatively small width w (e.g., in the range of 2 mm-4 mm) to accommodate the electrodes 30a, 30b (taking into account the spacing s therebetween) on the limited width of the probe body 42, but large enough, such that the exposed outer surfaces of the electrodes 30a, 30b do not have excessive current density when activated. The electrodes 30a, 30b may protrude a certain distance (e.g., 1 mm) from the surface of the probe body 42. Preferably, the transvaginal stimulation device 12 comprises no additional electrodes laterally disposed relative to the pair of electrodes 30a, 30b, such that the pair of electrodes 30a, 30b can convey electrical stimulation energy to the targeted periurethral structure component (in this case, the mid-urethral striated sphincter muscle 110) in a more focused manner. While the current flowing through electrodes 30a, 30b may be similar to prior art pelvic floor stimulators, the transvaginal stimulation device 12 can stimulate the mid-urethral striated sphincter muscle 110 with considerably lower voltage and power because the mid-urethral striated sphincter muscle 110 has a lower impedance than the pelvic floor muscles.

Notably, since the location of each of the electrodes 30a, 30b of the transvaginal stimulation device 12 illustrated in FIGS. 6A-6F is fixed relative to the probe body 42, it is important that the electrodes 30a, 30b be axially aligned with the mid-urethral striated sphincter muscle 110 once the transvaginal stimulation device 12 is properly seated within the vaginal cavity 124 of the patient 100. As such, the axial centers of the electrodes 30a, 30b should be located the proper distance d2 on the probe body 42 relative to the waist 58 of the probe body 42, as illustrated in FIG. 6E. For example, the distance d1 between the axial centers of the electrodes 30a, 30b and the waist 58 of the probe body 42 can be in the range of 1.5 cm-2.5 cm.

To ensure proper seating of the waist 58 of the probe body 42 in the introitus 125 of the patient 100, the extraction mechanism 44 of the transvaginal stimulation device 12 may alternatively be rigid. In this case, because the extraction mechanism 44 is rigid, abutment between the distal facing surface 62 of the fingerhold 50 and the pubic bone 126, as illustrated in FIG. 3A, prevents the probe body 42 from being inserted too far into the vaginal cavity 124, which would otherwise result in improper seating of the transvaginal stimulation device 12 within the vaginal cavity 124 of the patient 100 relative to the urethra 104. It should be appreciated that the distance between the pubic bone 126 and the urethral meatus (i.e., the opening to the urethra 104) is generally consistent between patients, and thus, the extraction mechanism 44 allows the electrodes 30a, 30b to be axially located relative to the urethra 104, as opposed to the vaginal anatomy of the patient 100, thereby more accurately placing the electrodes 30a, 30b adjacent the mid-urethral striated sphincter muscle 110 of the patient 100. It is preferred that the fingerhold 44 be located at the 12 o'clock position, since the tissue thickness at the 12 o'clock position in the area of the pubic bone 126 is consistent between patients, as opposed to other positions, e.g., the 10 o'clock or 2 o'clock positions where the tissue thickness may vary between patients.

Figure 9A:
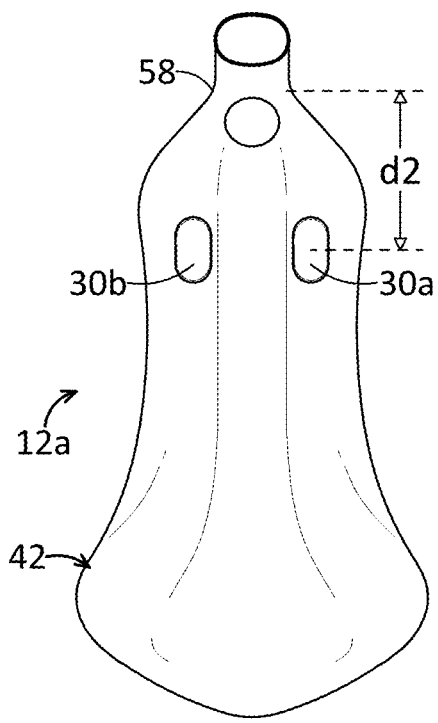
FIGS. 9A-9C are top views of the transvaginal stimulation device of FIG. 6E with different electrode positions.
Figure 9B:
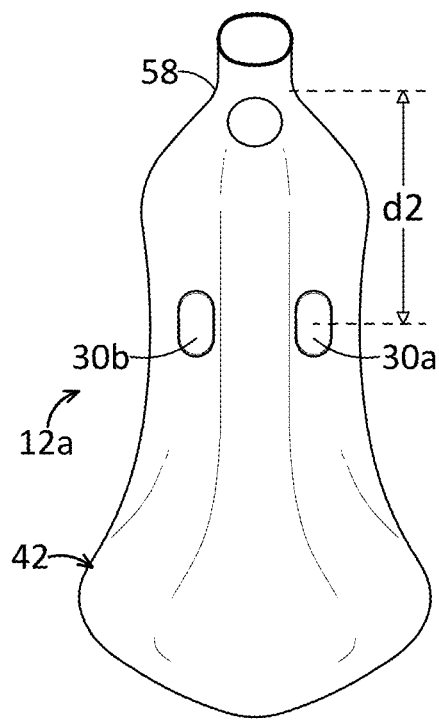
Figure 9C:
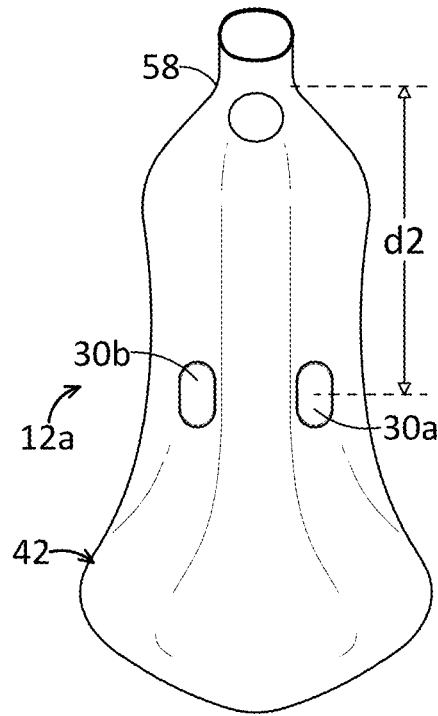

In an optional embodiment illustrated in FIG. 9A-9C, multiple transvaginal stimulation devices 12a-12c having different distances d2 between the electrodes 30a, 30b and the waist 58 of the probe body 42 may be provided (e.g., the distances d2 may range from 1.5 cm to 2.5 cm), such that the electrodes 30a, 30b of at least one of the transvaginal stimulation devices 12a-12c are axially aligned with the mid-urethral striated sphincter muscle 110 of the patient 100 when the respective transvaginal stimulation device 12 is properly seated within the vaginal cavity 124 of the patient 100. Thus, one of the stimulation devices 12a-12c may be judiciously selected, such that distance d2 between the electrode 30a, 30b and the waist 58 matches the distance between the introitus 125 of the vaginal cavity 124 (shown in FIG. 3A) and the mid-urethral striated sphincter muscle 110.

Figure 10A:
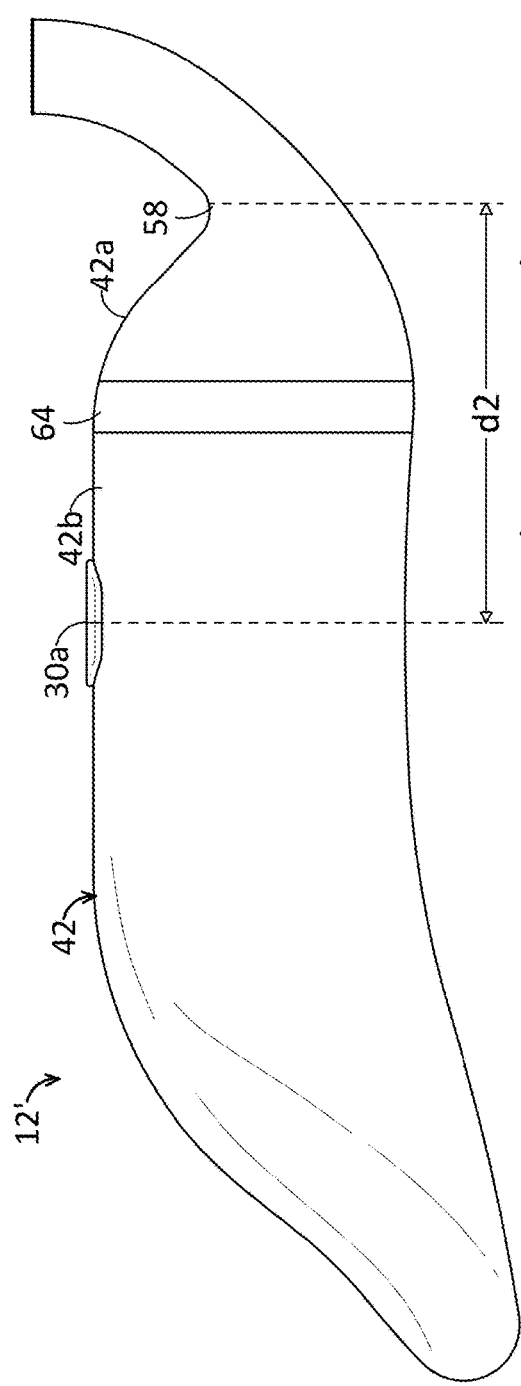
FIGS. 10A and 10B are profile views of yet another embodiment of a transvaginal stimulation device for use in the SUI treatment system of FIG. 2.
Figure 10B:
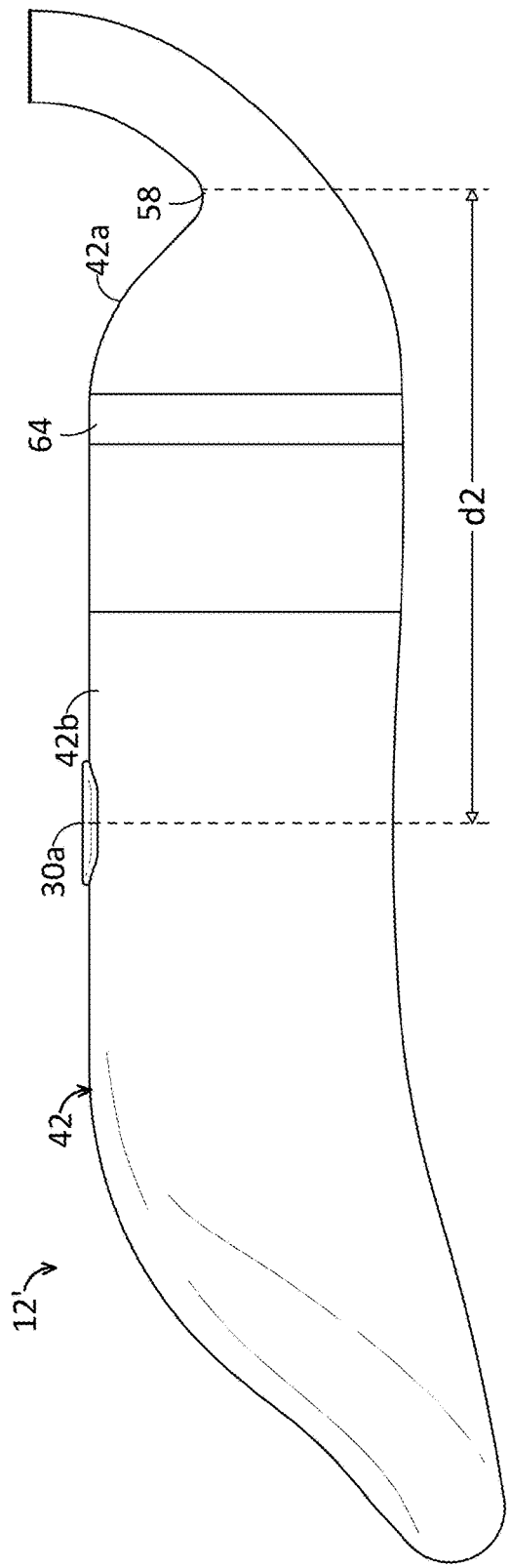

Referring to FIGS. 10A and 10B, another embodiment of a transvaginal stimulation device 12' has a telescoping arrangement. In particular, probe body 42 of the transvaginal stimulation 12' is divided into two telescoping proximal and distal probe bodies 42a, 42b that can be displayed relative to each other. The transvaginal device 12' comprises a locking mechanism 64 (e.g., a collet feature or collar) that can be manipulated to lock the axial displacement between the proximal and distal probe bodies 42a, 42b to ensure that the transvaginal stimulation device 12' remains at the desired length. Thus, the distance d2 between the electrodes 30a, 30b and the waist 58 of the probe body 42 may be varied (e.g., the distances d2 may range from 1.5 cm to 2.5 cm) by displacing and then locking the proximal and distal probe bodies 42a, 42b relative to each other to match the distance between the introitus 125 of the vaginal cavity 124 (shown in FIG. 3A) and the mid-urethral striated sphincter muscle 110, thereby facilitating axial alignment between the electrodes 30a, 30b and the mid-urethral striated sphincter muscle 110 of the patient 100 when the respective transvaginal stimulation device 12' is properly seated within the vaginal cavity 124 of the patient 100.

Figure 11A:
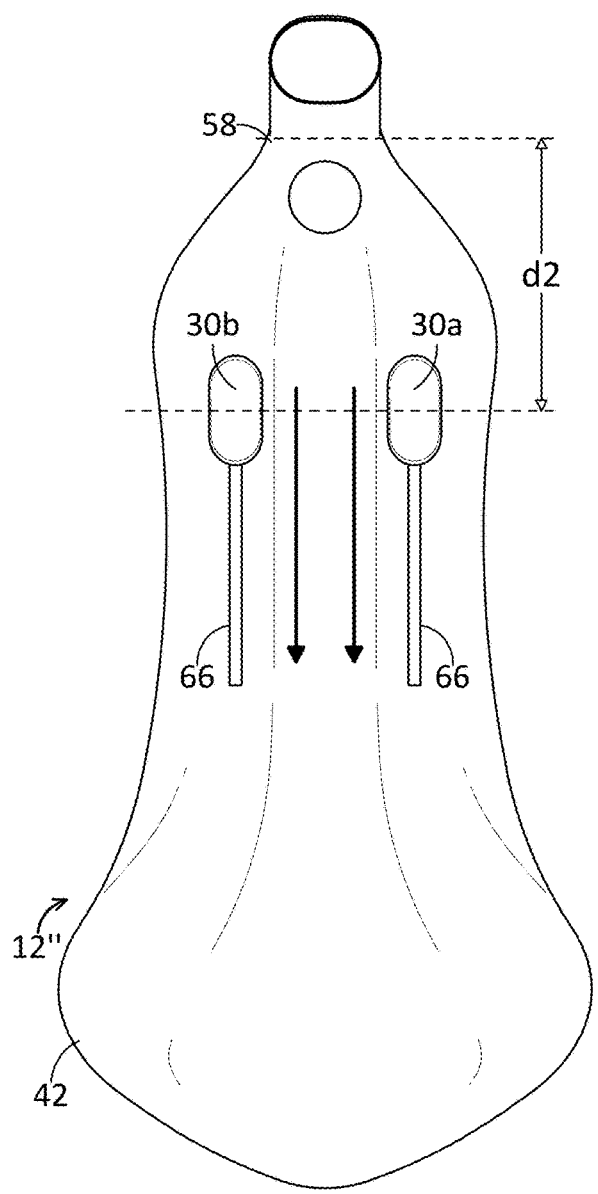
FIGS. 11A and 11B are top views of yet another embodiment of a transvaginal stimulation device for use in the SUI treatment system of FIG. 2.
Figure 11B:
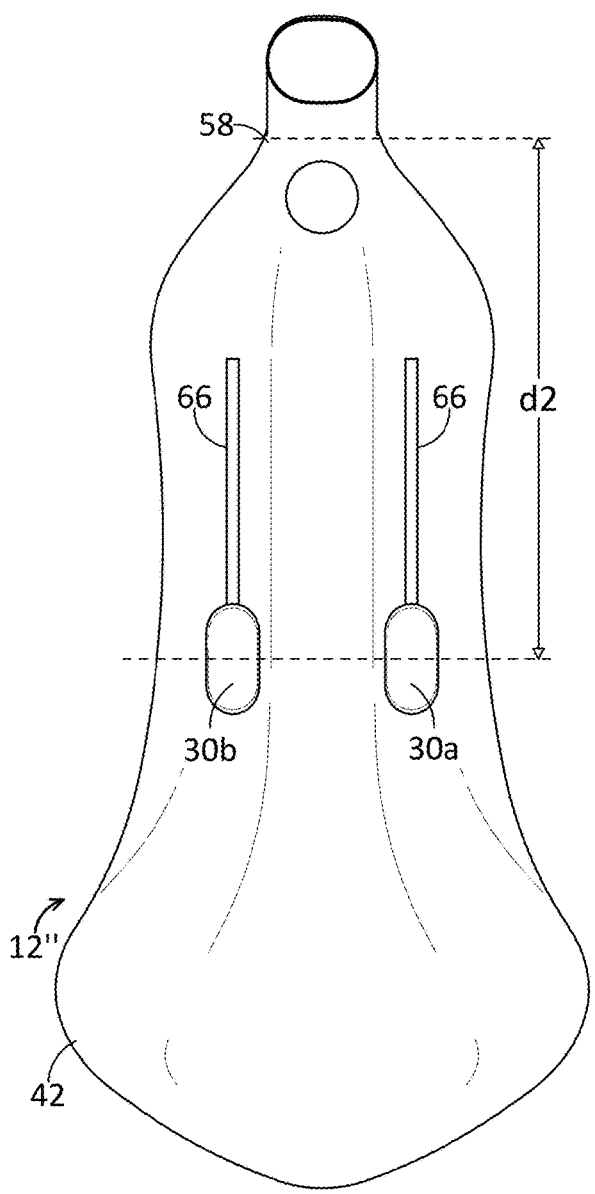

Referring to FIGS. 11A and 11B, still another embodiment of a transvaginal stimulation device 12" comprises moveable electrodes 32a, 32b having mechanically variable axial locations, such that the electrodes 32a, 32b may be axially aligned with the periurethral structural components of the patient 100. For example, the transvaginal stimulation device 12" may have interfacing features, such as a J-channel 66 between the electrodes 32a, 32b and the probe body 42 that allows the electrodes 32a, 32b to be incrementally adjusted and locked in the axial direction relative to the probe body 42, e.g., every 5 mm. Thus, the distance d2 between the electrodes 30a, 30b and the waist 58 of the probe body 42 vary be varied (e.g., the distances d2 may range from 1.5 cm to 2.5 cm) by displacing and locking the electrodes 32a, 32b to match the distance between the introitus 125 of the vaginal cavity 124 (shown in FIG. 3A) and the mid-urethral striated sphincter muscle 110, thereby facilitating axial alignment between the electrodes 30a, 30b and the mid-urethral striated sphincter muscle 110 of the patient 100 when the respective transvaginal stimulation device 12" is properly seated within the vaginal cavity 124 of the patient 100.

Figure 12:
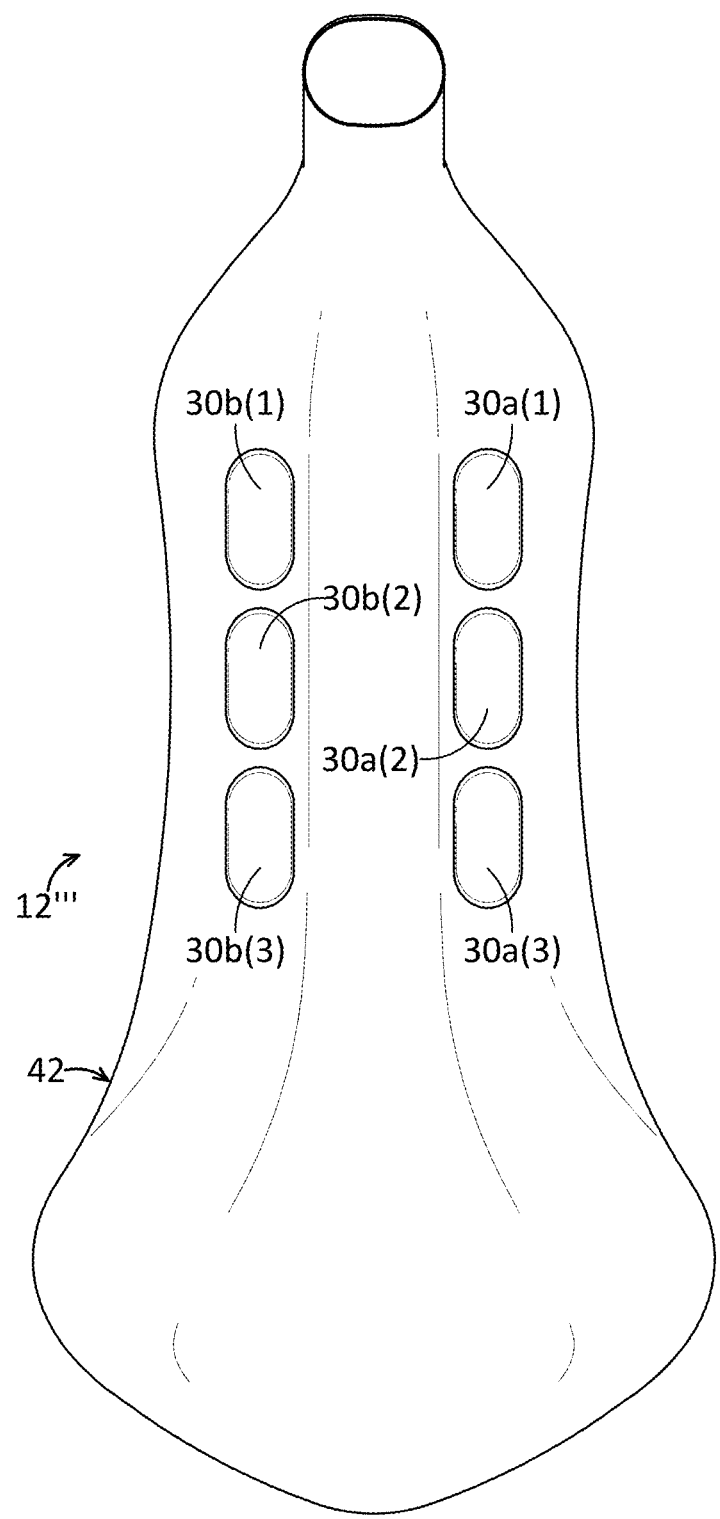
FIG. 12 is a top view of yet another embodiment of a transvaginal stimulation device for use in the SUI treatment system of FIG. 2.

Although each of the transvaginal stimulation devices 12, 12', and 12" illustrated in FIGS. 6-12 has a single pair of electrodes 30a, 30b, yet another embodiment of a transvaginal stimulation device 12" may comprise a pair of linear arrays of electrodes 30a(1)-(3), 30b(1)-(3), as illustrated in FIG. 12. Significantly, pairs of electrodes 30a(1)(3), 30b(1)-(3) may be activated, such that the location of stimulation along the urethra 104 can be cranio-caudally varied, even though the physical location of the transvaginal stimulation device 12, and the electrodes 30a(1)-(3), 30b(1)-(3), is fixed in the vaginal cavity 124 of the patient 100.

A pair of electrodes 30a(1)-(3), 30b(1)-(3) may be selectively activated to craniocaudally vary the location (either proximally or distally) of stimulation along the urethra 104. It is preferred that any selected pair of electrodes be activated as transverse (i.e., displaced from each other along the transverse axis) bipolar electrode combinations; i.e., the electrodes in one of the electrode arrays L, R be activated as anodes, and the electrodes in the other of the electrode arrays L, R be activated as cathodes, thereby providing the most effective bipolar stimulation to the circumferential striated muscle 110.

Figure 13A:
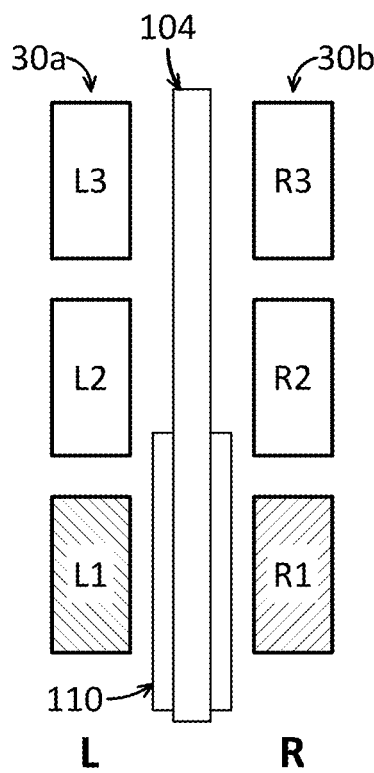
FIGS. 13A-13P are plan views of the linear electrode arrays of the transvaginal stimulation device of FIG. 12, wherein electrodes can be selectively activated to stimulate targeted areas of the periurethral structure components.
Figure 13B:
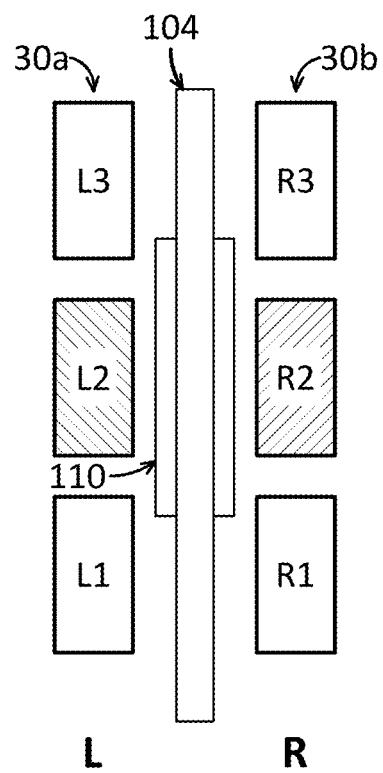
Figure 13C:
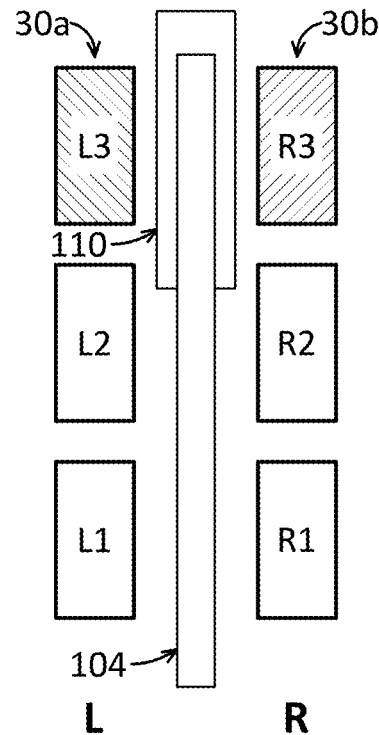

For example, as illustrated in FIGS. 13A-13C, different traverse bipolar pairs of electrodes in the linear array of electrodes 30a(1)-(3), 30b(1)-(3) (respectively designated "L1-L3" and "R1-R3") can be activated to vary the location of stimulation relative to the urethra 104 in order to focus the stimulation over the circumferential striated muscle 110. For example, one transverse bipolar pair of electrodes in the linear electrode arrays L, R (e.g., electrode L1 versus electrode R1) may be activated for a more cranial stimulation location (i.e., a more caudally located mid-urethral striated sphincter muscle 110), as illustrated in FIG. 13A; another transverse bipolar pair of electrodes in the linear electrode arrays L, R (e.g., electrode L2 versus electrode R2) may be activated for a medial stimulation location, as illustrated in FIG. 13B; and still another transverse bipolar pair of electrodes in the linear electrode arrays L, R (e.g., electrode L3 versus electrode R3) may be activated for a more caudal stimulation location, as illustrated in FIG. 13C.

In an optional technique, the different transverse bipolar pairs of electrodes L1-L3, R1-R3 may be cycled to actively move the stimulation location in the cranial-caudal direction relative to the urethral 104 by sequentially activating transverse bipolar electrode pairs in a wave in a single stimulation regimen. For example, the transverse bipolar electrode pairs may be sequentially activated in the caudal direction (e.g., by activating electrode L1 versus electrode R1, then electrode L2 versus electrode R2, and then electrode L3 versus electrode R3) and/or in the cranial direction (by activating electrode L3 versus electrode R3, then electrode L2 versus electrode R2, then electrode L3 versus electrode R3). The transverse bipolar pairs of electrodes L1-L3, R1-R3 may be activated in any order, and one pair of electrodes may be activated more or less than another transverse bipolar pair of electrodes, as long as each electrode pair is activated at least once in the single stimulation regimen.

While it is believed that specifically targeting the mid-urethral striated sphincter muscle 110 for stimulation is the most effective way to treat SUI of the patient 100, it should be appreciated that there may be circumstances where supplemental stimulation of other periurethral structural components of the patient 100 (e.g., the circumferential smooth muscle 112 and/or the longitudinal smooth muscle 114) may be desirable. In this case, the stimulation regimen may not be limited to the activation of a single transverse pair of electrodes 30a, 30b in a bipolar fashion.

Figure 13D:
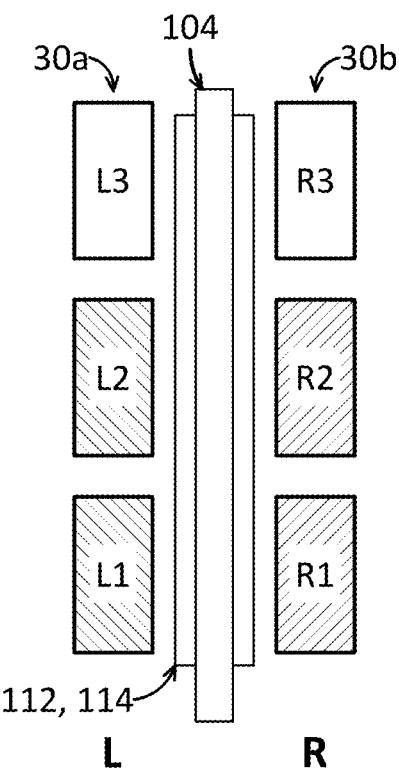
Figure 13E:
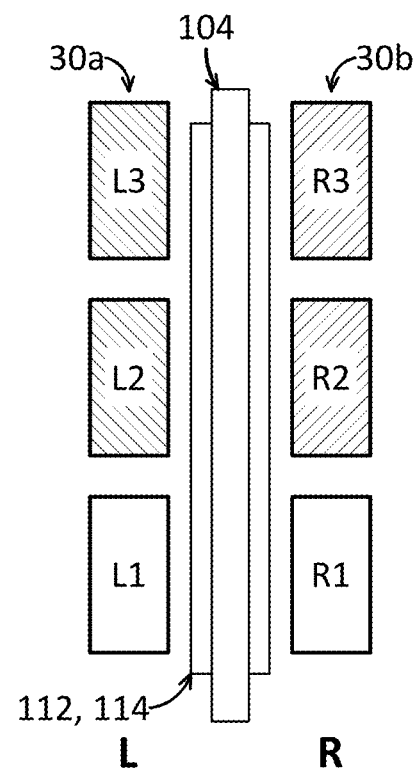
Figure 13F:
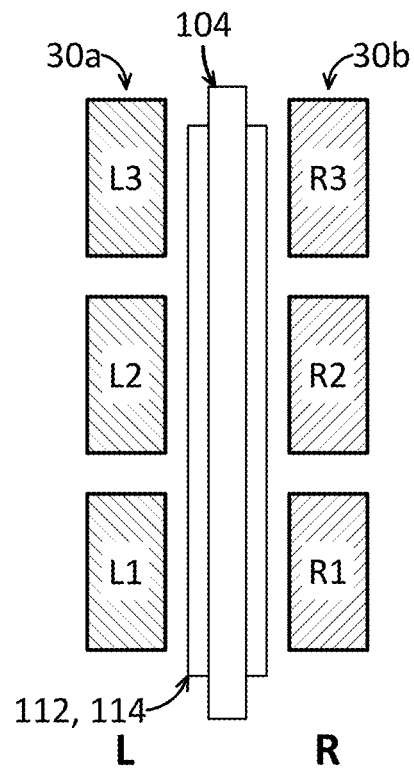

In one embodiment, transverse multipolar subsets of electrodes L1-L3, R1-R3 may be activated, as illustrated in FIGS. 13D-13F, thereby providing the most effective stimulation to both the circumferential striated muscle 110 and the circumferential smooth muscle 112. For example, two electrodes in the linear electrode array L may be activated with one polarization, and two electrodes in the linear electrode array R may be activated with another polarization (e.g., by activating electrodes L1+L2 versus electrodes R1+R2, as shown in FIG. 13D, or by activating electrodes L2+L3 versus electrodes R2+R3, as shown in FIG. 13E). As another example, three electrodes in the linear electrode array L may be activated with one polarization, and three electrodes in the linear electrode array R may be activated with another polarization (in this case, by activating electrodes L1+L2+L3 versus electrodes R1+R2+R3), as shown in FIG. 13F.

Figure 13G:
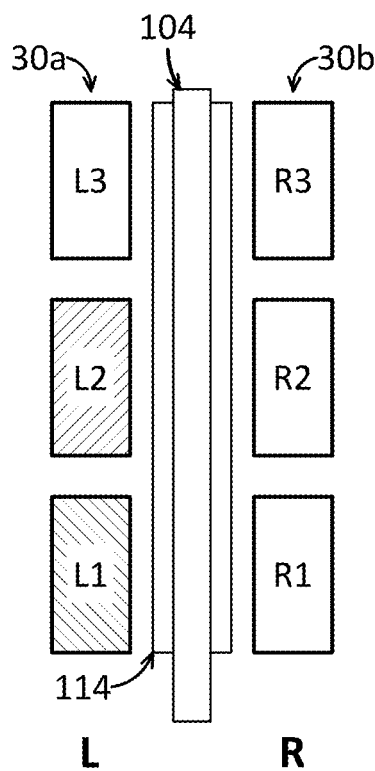
Figure 13H:
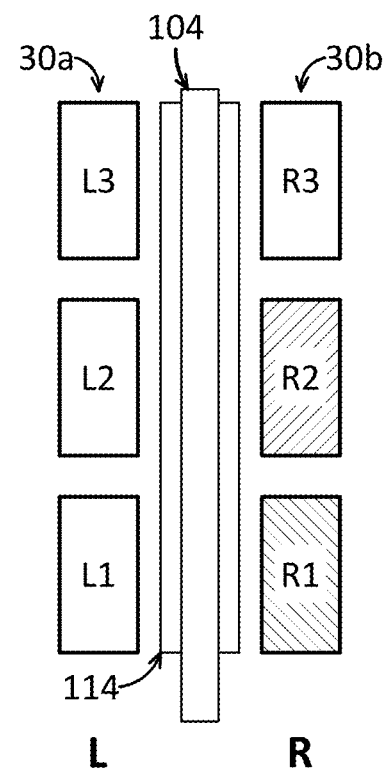
Figure 13I:
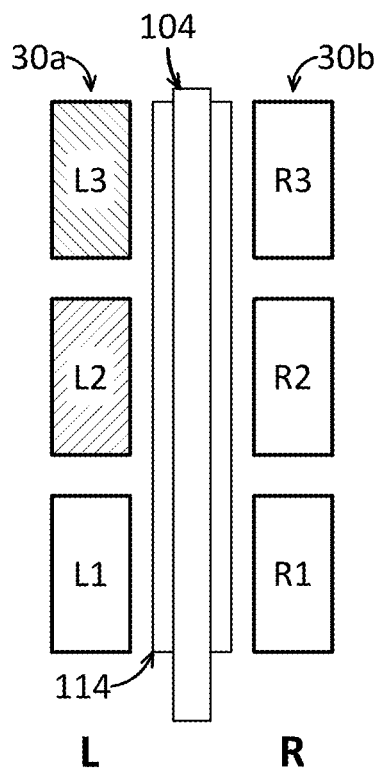
Figure 13J:
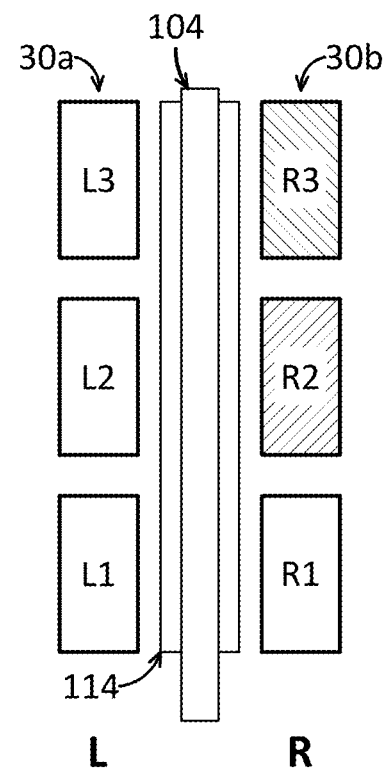
Figure 13K:
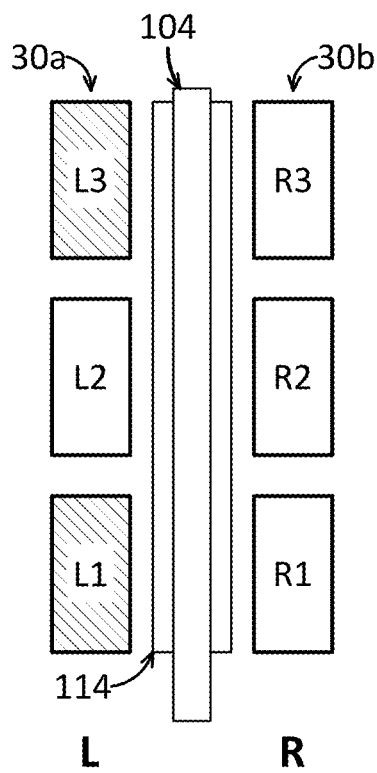
Figure 13L:
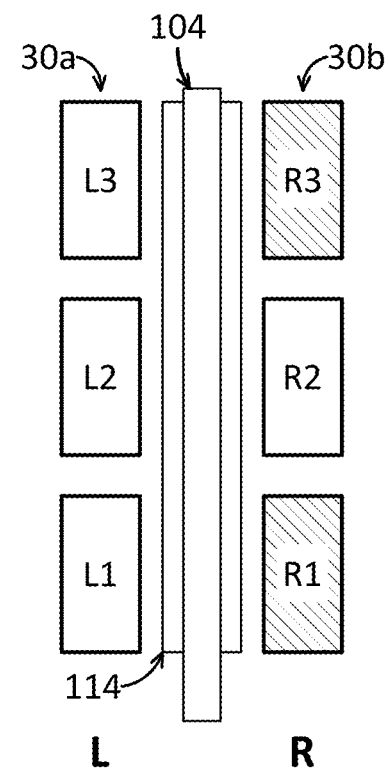
Figure 13M:
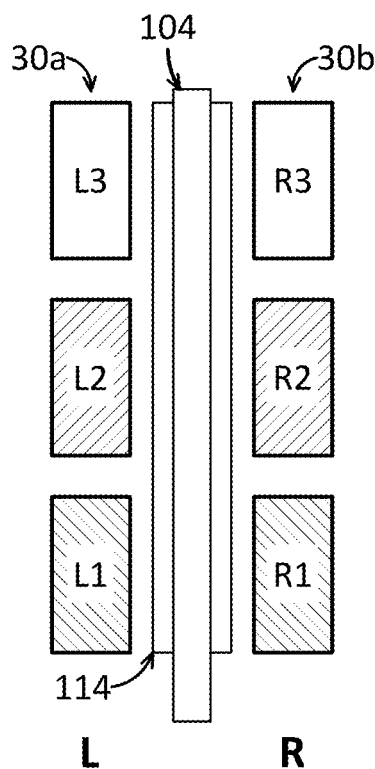

In another embodiment, longitudinal (i.e., displaced from each other along the longitudinal axis) multipolar subsets of electrodes L1-L3, R1-R3 may be activated, as illustrated in FIGS. 13G-13L, thereby providing the most effective stimulation to the longitudinal smooth muscle 114. For example, one longitudinal bipolar pair of electrodes in the linear electrode array L (e.g., electrode L1 versus electrode L2) may be activated, as illustrated in FIG. 13G; another longitudinal bipolar pair of electrodes in the linear electrode array R (e.g., electrode R1 versus electrode R2) may be activated, as illustrated in FIG. 13H; still another longitudinal bipolar pair of electrodes in the linear electrode array L (e.g., electrode L2 versus electrode L3) may be activated, as illustrated in FIG. 13I; yet another longitudinal bipolar pair of electrodes in the linear electrode array L (e.g., electrode R2 versus electrode R3) may be activated, as illustrated in FIG. 13J; yet another longitudinal bipolar pair of electrodes in the linear electrode array L (e.g., electrode L1 versus electrode L3) may be activated, as illustrated in FIG. 13K; and yet another longitudinal bipolar pair of electrodes in the linear electrode array R (e.g., electrode R1 versus electrode R3) may be activated, as illustrated in FIG. 13L. As another example, two electrodes respectively in the linear electrode arrays L, R may be activated with one polarization, and two electrodes in the linear electrode arrays L, R may be activated with another polarization (e.g., by activating electrodes L1+R1 versus electrodes L2+R2, as shown in FIG.

Figure 13N:
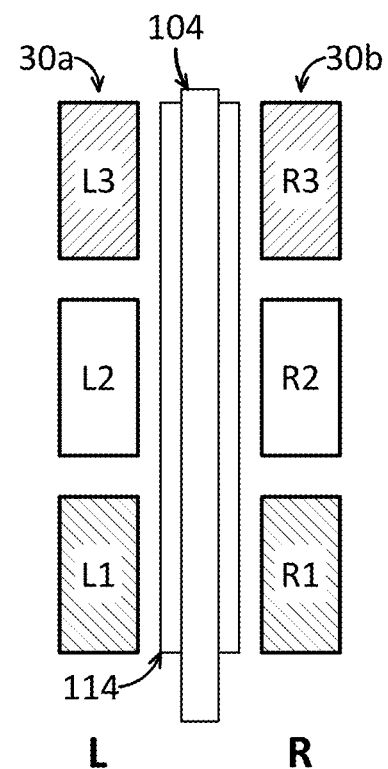

13M, or by activating electrodes L1+R1 versus electrodes L3+R3, as shown in FIG. 13N).

Figure 13O:
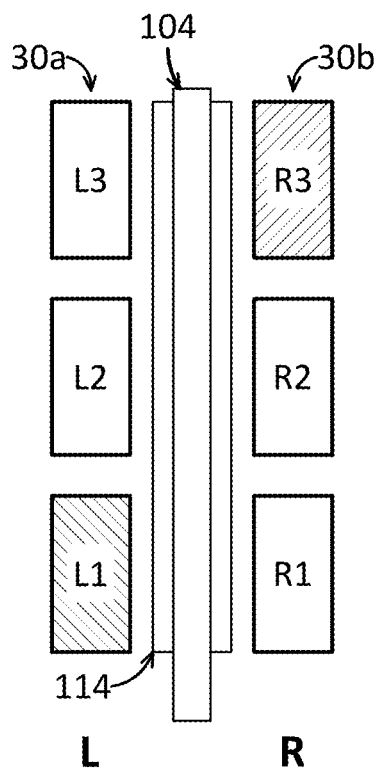
Figure 13P:
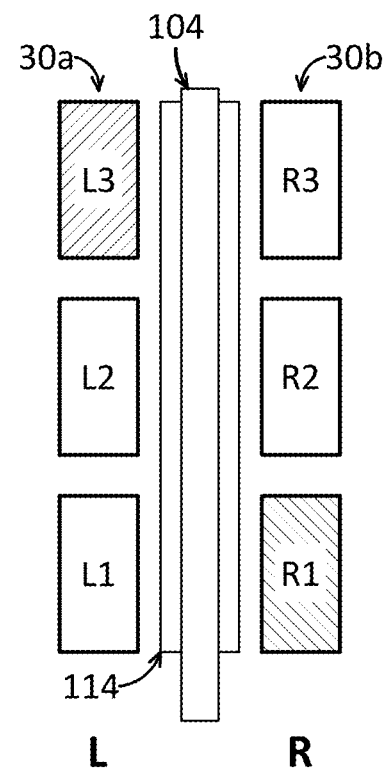

Although bipolar pairs of electrodes have been illustrated as being orthogonal (horizontally and vertically disposed), bipolar pairs of electrodes may be diagonally disposed relative to each other. For example, one diagonal bipolar pair of electrodes in the linear electrode arrays L, R (e.g., electrode L1 versus electrode R3) may be activated, as illustrated in FIG. 13O; and another diagonal bipolar pair of electrodes in the linear electrode arrays L, R (e.g., electrode L3 versus R1) may be activated, as illustrated in FIG. 13P.

Figure 14:
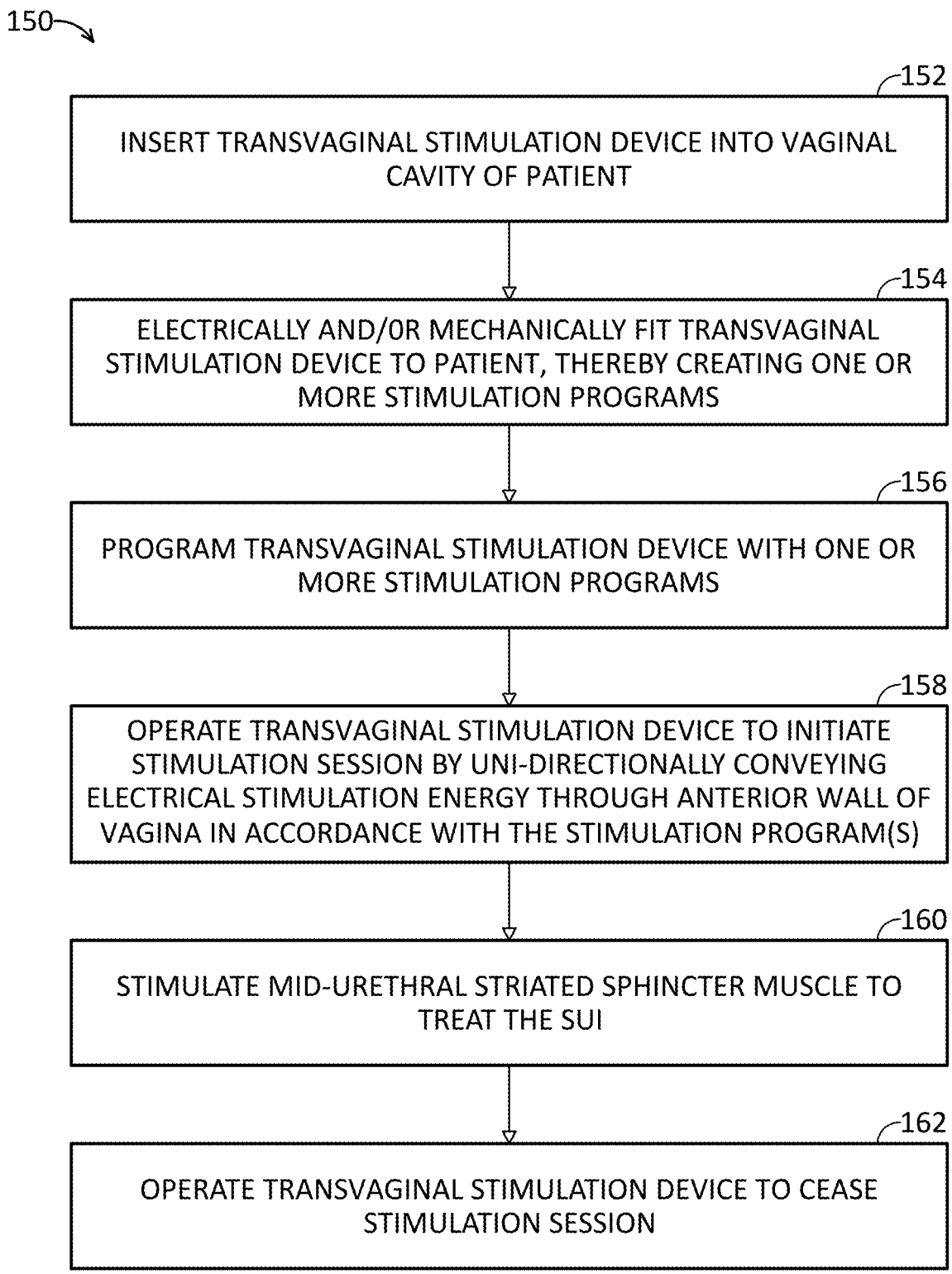
FIG. 14 is a flow diagram illustrating one method of using the SUI treatment system of FIG. 2 to treat SUI in a patient.

Having described the structure and function of the SUI treatment system 10, one method 150 of using the SUI treatment system to treat SUI in the patient 100 will now be described. Referring to FIG. 14, the transvaginal stimulation device 12 (or alternatively, any of the transvaginal stimulation devices 12, 12", or 12") is inserted into the vaginal cavity 124 of the patient 100, such that scoop 60 conforms to the posteriorly angled cranial end of the vaginal cavity 124 when the probe body 42 is fully disposed in the vaginal cavity 124, and the levator ani muscles 132 of the female patient 100 are disposed adjacent to the mid-region 47 between the flattened scoop 60 and the shoulders 56, as illustrated in FIGS. 3A, 8A and 8B (step 152). Thus, the transvaginal stimulation device 12 will be securely seated and retained within the vaginal cavity 124, while the stimulating side 52a of the probe body 42 of the transvaginal stimulation device 12 contacts the anterior wall 122 of the vagina 120, such that the electrodes 30a, 30b face the urethra 104. Proper seating and orientation of the transvaginal stimulation device 12 can be confirmed by approximating the pubic bone 126 of the female patient 100 with the proximal surface of the fingerhold 62 of the extraction mechanism 44.

Next, the transvaginal stimulation device 12 is mechanically and/or electrically fitted to the patient 100 to optimize treatment of the SUI (step 154). As stated above, maximum urethral closure pressure of a patient can be considered a good measure of optimized SUI treatment. As such, biofeedback in the form of urethral closure pressure measurements of the patient 100 can be used while mechanically and/or electrically fitting transvaginal stimulation device 12 to the patient 100, such that one or more stimulation regimens (defining the stimulation parameters and axial electrode placement relative to the mid-urethral striated sphincter muscle 110 of the patient 100 (see FIG. 1A)) can be determined. In general, it is desirable to select stimulation regimens that achieve a sufficient maximum closure pressure, while minimizing the current density on the electrodes 30a, 30b.

As one example of fitting the transvaginal stimulation device 12, the clinician programmer 14 may be operated to convey electrical stimulation energy from the electrodes 30a, 30b of the inserted transvaginal device 12, while varying any one or more electrical stimulation parameters (e.g., varying the pulse width in the range of 0.1 ms-2 ms and/or varying the pulse frequency in the range of 20 Hz-60 Hz and/or varying the magnitude in the range of 1 mA-50 mA), to define one or more efficacious stimulation programs.

In the case where different sized transvaginal stimulation devices 12 are available (FIGS. 9A-9C), each different transvaginal stimulation device 12 may be inserted into the vaginal cavity 124 of the patient 100 to determine the optimally sized transvaginal stimulation device 12. For example, the transvaginal stimulation device 12 having the proper distance between the electrodes 30a, 30b and the waist 58 of the probe body 42, such that the electrodes 30a, 30b are coincident with the mid-urethral striated sphincter muscle 110 (i.e., the transvaginal stimulation device 12 that results in maximum urethral closure pressure) may be selected.

In the case where the telescoping transvaginal stimulation device 12 is used (FIGS. 10A and 10B), the proximal and distal body portions 42a, 42b may be axially displaced relative to each other to vary the distance between the electrodes 30a, 30b and the waist 58 of the probe body 42, such that the electrodes 30a, 30b are coincident with the mid-urethral striated sphincter muscle 110 (i.e., the transvaginal stimulation device 12 that results in maximum urethral closure pressure). The locking mechanism 64 can then be locked to affix the electrodes 30a, 30b relative to the probe body 42.

In the case where the transvaginal stimulation device 12" is used (FIGS. 11A and 11B), the electrodes 30a, 30b may be axially adjusted relative to the probe body 42 to vary the distance between the electrodes 30a, 30b and the waist 58 of the probe body 42, such that the electrodes 30a, 30b are coincident with the mid-urethral striated sphincter muscle 110 (i.e., the transvaginal stimulation device 12 that results in maximum urethral closure pressure).

In the case where the transvaginal stimulation device 12" is used (FIG. 12), different pairs of the electrode 30a, 30b can be activated to determine the pair of electrodes 30a, 30b that is coincident with the mid-urethral striated sphincter muscle 110 (i.e., the transvaginal stimulation device 12 that results in maximum urethral closure pressure). The clinician programmer 14 may be operated to automatically sequence through various combinations of electrode pairs and other electrical stimulation parameters while maintaining the electrical current at an effective, but comfortable, level, e.g., in the range of 1 mA-50 mA. The frequency of the electrical stimulation energy may have a range of, e.g., 5 Hz-50 Hz.

Next, the clinician programmer 14 is operated to program the transvaginal stimulation device 12 with optimized stimulation program(s) (defining the location of the electrodes 30a, 30b in the case of the transvaginal stimulation device 12", as well as the pulse width, pulse frequency, and pulse amplitude (step 156). The transvaginal stimulation device 12 may then be operated to initiate stimulation session by transvaginally conveying electrical stimulation energy unidirectionally through the anterior wall 122 of the vagina 120 in accordance with one or more stimulation programs. For example, the patient 100 may operate the patient controller 16 (or alternatively, the minimal UI 46) to activate the transvaginal stimulation device 12 and select the stimulation program(s). During the stimulation session, the mid-urethral striated sphincter muscle 110 is stimulated to treat the SUI of the patient 100 without substantially stimulating pelvic floor muscles of the patient 100 (step 160). The transvaginal stimulation device 12 may then automatically terminate the stimulation session, e.g., in accordance with a predetermined cycle (step 162). Alternatively, the transvaginal stimulation device 12 may be manually terminated, e.g., by operating the patient controller 16 (or alternatively, the minimal UI 46) to deactivate the transvaginal stimulation device 12. It is contemplated that the patient 100 will require approximately 15 minutes of treatment time every day for at least 8-12 weeks to hypertrophy the periurethral structural components, and more particularly, the mid-urethral striated sphincter muscle 110.

Although particular embodiments of the disclosed inventions have been shown and described herein, it will be understood by those skilled in the art that they are not intended to limit the disclosed inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

In addition to the appended claims, additional specific embodiments of the disclosed inventions, including in each case all essential limitations, include without limitation:

Aspect 1. A transvaginal stimulation device, comprising: a probe body sized to fit entirely within a vaginal cavity of a female patient, the probe body having a length extending in a longitudinal direction, a width extending in a lateral direction, and a depth being perpendicular to the length and width, the probe body having a stimulating side defined by the length and the width of the probe body; and a transverse bipolar pair of electrodes disposed on the stimulating side of the probe body and laterally spaced from each other, wherein the pair of electrodes have an edge-to-edge lateral spacing in a range between 5 mm and 25 mm.

Aspect 2. The transvaginal stimulation device of aspect 1, wherein the probe body has a concave region longitudinally extending along the stimulating side of the probe body, and wherein the concave region is shaped to cradle a urethra carina of the female patient when the probe body is positioned in a vaginal cavity.

Aspect 3. The transvaginal stimulation device of aspects 1 or 2, wherein the probe body is rigid or semi-rigid.

Aspect 4. The transvaginal stimulation device of any of aspects 1 to 3, wherein the length of the probe body is in a range between 4 cm and 8 cm.

Aspect 5. The transvaginal stimulation device of any of aspects 1 to 4, wherein the width of the probe body has a greatest lateral extent that is greater than the depth of the probe body.

Aspect 6. The transvaginal stimulation device of any of aspects 1 to 5, wherein a distal region of the probe body laterally flares outward in a distal direction from a mid-region of the probe body to form a flattened scoop.

Aspect 7. The transvaginal stimulation device of aspect 6, wherein the flattened scoop angles away from the stimulating side of the probe body.

Aspect 8. The transvaginal stimulation device of aspect 6 or 7, wherein a proximal region of the probe body laterally flares outward in a proximal direction from the mid-region to form shoulders.

Aspect 9. The transvaginal stimulation device of aspect 8, wherein the mid-region of the probe body is sized and configured, such that when the probe body is fully disposed in the vaginal cavity, levator ani muscles of the female patient are disposed adjacent to the mid-region between the flattened scoop and the shoulders.

Aspect 10. The transvaginal stimulation device of any of aspects 1 to 7, wherein the transvaginal stimulation device is free of any electrodes laterally disposed relative to the pair of electrodes.

Aspect 11. The transvaginal stimulation device of any of aspects 1 to 8, wherein the probe body has a non-stimulating side opposite the stimulating side of the probe body, wherein the non-stimulating side of the probe body is free of any electrode.

Aspect 12. The transvaginal stimulation device of any of aspects to 10, wherein each electrode of the transverse bipolar pair of electrodes has an elongated shape, and wherein the electrodes are disposed parallel to each other.

Aspect 13. The transvaginal stimulation device of aspect 12, wherein the transverse bipolar pair of electrodes respectively have lengths extending along the length of the probe body in a range between 4 mm and 12 mm.

Aspect 14. The transvaginal stimulation device of aspects 12 or 13, wherein the pair of electrodes have an edge-to-edge lateral spacing in a range between 10 mm and 20 mm.

Aspect 15. The transvaginal stimulation device of any of aspects 1 to 14, wherein the transverse bipolar pair of electrodes includes a first electrode having a first flat tissue contacting surface and a second electrode having a second flat tissue contacting surface tissue.

Aspect 16. The transvaginal stimulation device of aspect 15, wherein the first tissue contacting surface and the second tissue contacting surface form an angle within a range between 160° and 200°.

Aspect 17. The transvaginal stimulation device of aspect 15, wherein the first tissue contacting surface and the second tissue contacting surface form an angle within a range between 170° and 190°.

Aspect 18. The transvaginal stimulation device of aspect 15, wherein the first tissue contacting surface and the second tissue contacting surface form an angle of 180°.

Aspect 19. The transvaginal stimulation device of any of aspects 1 to 18, wherein the transverse bipolar pair of electrodes are respectively positioned on the probe body, so that when the probe body is positioned in a vaginal cavity of the female patient, bipolar electrical stimulation energy delivered between the pair of electrodes stimulates at least one muscle of a urethral sphincter of the female patient without substantially stimulating pelvic floor muscles of the female patient.

Aspect 20. The transvaginal stimulation device of aspect 19, wherein the at least one muscle of the urethral sphincter comprises a mid-urethral striated sphincter muscle.

Aspect 21. The transvaginal stimulation device of either aspect 19 or 20, wherein the at least one muscle of the urethral sphincter comprises one or both of a circumferential smooth muscle and a longitudinal smooth muscle.

Aspect 22. The transvaginal stimulation device of any of aspects 1 to 21, further comprising stimulation circuitry contained within the probe body, the stimulation circuitry configured for delivering bipolar electrical stimulation energy between the pair of electrodes.

Aspect 23. The transvaginal stimulation device of any of aspects 19 to 21, further comprising a user interface disposed on the probe body, the user interface configured for deactivating the stimulation circuitry.

Aspect 24. The transvaginal stimulation device of any of aspects 1 to 23, further comprising an extraction element extending proximally from the probe body configured for being grasped to extract the probe body from the vaginal cavity of the female patient.

Aspect 25. The transvaginal stimulation device of aspect 24, wherein the extraction mechanism comprises a finger-hold having a proximal surface configured for approximating a pubic bone of the female patient when the probe body is fully disposed in the vaginal cavity of the female patient.

Aspect 26. The transvaginal stimulation device of any of aspects 1 to 25, further comprising a pair of linear electrode arrays extending along the length of the probe body, the pair of linear electrode arrays respectively comprising the pair of electrodes.

Aspect 27. The transvaginal stimulation device of aspect 26, wherein different subsets of electrodes of the respective pair of electrodes arrays are configured for being selectively activated.

Aspect 28. The transvaginal stimulation device of aspect 27, wherein the different subsets of electrodes comprise different bipolar pairs of electrodes.

Aspect 29. The transvaginal stimulation device of aspect 28, wherein the different bipolar pairs of electrodes are transverse bipolar pairs of electrodes.

Aspect 30. The transvaginal stimulation device of aspect 27, wherein the different bipolar pairs of electrodes are longitudinal bipolar pairs of electrodes.

Aspect 31. The transvaginal stimulation device of any of aspects 27 to 30, wherein the different subsets of electrodes are configured for being cyclically activated one-at-a-time.

Aspect 32. The transvaginal stimulation device of any of aspects 1 to 25, wherein a proximal region of the probe body comprises shoulders that laterally taper inward in a proximal direction to form a waist.

Aspect 33. The transvaginal stimulation device of aspect 32, wherein an axial center of the transverse bipolar pair of electrodes is distally spaced from the waist a distance in a range between 1.5 cm and 2.5 cm.

Aspect 34. The transvaginal stimulation device of aspect 33, wherein the probe body comprises telescoping proximal and distal probe bodies configured for being axially displaced relative to each other, such that a distance between the transverse bipolar pair of electrodes and the waist of the probe body can be varied.

Aspect 35. The transvaginal stimulation device of aspect 33, wherein the transverse bipolar pair of electrodes is configured for being axially displaced relative to the probe body, such that a distance between the pair of electrodes and the waist of the probe body can be varied.

Aspect 36. A transvaginal stimulation system, comprising the transvaginal stimulation device of any of aspects 1 to 34; and a clinician programmer configured for wirelessly programming the transvaginal stimulation device.

Aspect 37. The transvaginal stimulation system of aspect 32, wherein the transvaginal stimulation device further comprises a pair of linear arrays of electrodes respectively comprising the pair of electrodes, the pair of linear electrode arrays respectively extending along length of the probe body, and the clinician programmer is configured for: determining a stimulation regimen by selectively activating different pairs of electrodes respectively in the linear electrode arrays; and programming the transvaginal stimulation device with the stimulation regimen, such that the transvaginal stimulation device is configured for conveying electrical stimulation energy between the pair of electrodes in accordance with the stimulation regimen.

Aspect 38. The transvaginal stimulation system of aspect 36 or 37, further comprising a patient control configured for wirelessly controlling operation of the transvaginal stimulation device.

Aspect 39. A transvaginal stimulation device, comprising: a probe body sized to fit entirely within a vaginal cavity of a female patient, the probe body having a length extending in a longitudinal direction, a width extending in a lateral direction, and a depth being perpendicular to the length and width, the probe body having a stimulating side defined by the length and the width of the probe body, the probe body distally flaring outward from a mid-region to form a flattened scoop having a depth less than a depth of the mid-region; and a pair of electrodes disposed on the stimulating side of the probe body and laterally spaced from each other.

Aspect 40. The transvaginal stimulation device of aspect 39, wherein the probe body has a concave region longitudinally extending along the stimulating side of the probe body, and wherein the concave region is shaped to cradle a urethra carina of the female patient when the probe body is positioned in a vaginal cavity of the female patient.

Aspect 41. The transvaginal stimulation device of aspect 39 or 40, wherein the probe body is rigid or semi-rigid.

Aspect 42. The transvaginal stimulation device of any of aspects 39 to 41, wherein the length of the probe body is in a range between 4 cm and 8 cm.

Aspect 43. The transvaginal stimulation device of any of aspect 39 to 42, wherein the width of the probe body has a greatest lateral extent that is greater than the depth of the probe body.

Aspect 44. The transvaginal stimulation device of any of aspects 39 to 43, wherein the flattened scoop angles away from the stimulating side of the probe body.

Aspect 45. The transvaginal stimulation device of aspects 39 or 44, wherein a proximal region of the probe body laterally flares outward in a proximal direction from the mid-region to form shoulders.

Aspect 46. The transvaginal stimulation device of aspect 45, wherein the mid-region of the probe body is sized and configured, such that when the probe body is fully disposed in the vaginal cavity, levator ani muscles of the female patient are disposed adjacent to the mid-region between the flattened scoop and the shoulders.

Aspect 47. The transvaginal stimulation device of any of aspects 36 to 45, wherein the transvaginal stimulation device is free of any electrodes laterally disposed relative to the pair of electrodes.

Aspect 48. The transvaginal stimulation device of any of aspects 36 to 45, wherein the probe body has a non-stimulating side opposite the stimulating side of the probe body, wherein the non-stimulating side of the probe body is free of any electrode.

Aspect 49. The transvaginal stimulation device of any of aspects 36 to 50, wherein the pair of electrodes is a transverse pair of electrodes.

Aspect 50. The transvaginal stimulation device of aspect 49, wherein the pair of electrodes each have an elongated shape and are disposed parallel to each other.

Aspect 51. The transvaginal stimulation device of aspect 50, wherein the pair of electrodes respectively have lengths extending along the length of the probe body in a range between 4 mm and 12 mm.

Aspect 52. The transvaginal stimulation device of any of aspects 39 to 51, wherein the pair of electrodes have an edge-to-edge lateral spacing in a range between 10 mm and 20 mm.

Aspect 53. The transvaginal stimulation device of any of aspects 39 to 52, wherein the pair of electrodes includes a first electrode having a first flat tissue contacting surface and a second electrode having a second flat tissue contacting surface tissue.

Aspect 54. The transvaginal stimulation device of aspect 53, wherein the first tissue contacting surface and the second tissue contacting surface form an angle within a range between 160° and 200°.

Aspect 55. The transvaginal stimulation device of aspect 53, wherein the first tissue contacting surface and the second tissue contacting surface form an angle within a range between 170° and 190°.

Aspect 56. The transvaginal stimulation device of aspect 53, wherein the first tissue contacting surface and the second tissue contacting surface form an angle of 180°.

Aspect 57. The transvaginal stimulation device of any of aspects 39 to 58, wherein the pair of electrodes are respectively positioned on the probe body, so that when the probe body is positioned in a vaginal cavity of the female patient, bipolar electrical stimulation energy delivered between the pair of electrodes stimulates at least one muscle of a urethral sphincter of the female patient without substantially stimulating pelvic floor muscles of the female patient.

Aspect 58. The transvaginal stimulation device of aspect 57, wherein the at least one muscle of the urethral sphincter comprises a mid-urethral striated sphincter muscle.

Aspect 59. The transvaginal stimulation device of aspect 57 or 58, wherein the at least one muscle of the urethral sphincter comprises one or both of a circumferential smooth muscle and a longitudinal smooth muscle.

Aspect 60. The transvaginal stimulation device of any of aspects 39 to 59, further comprising stimulation circuitry contained within the probe body, the stimulation circuitry configured for delivering bipolar electrical stimulation energy between the pair of electrodes.

Aspect 61. The transvaginal stimulation device of aspect 60, further comprising a user interface disposed on the probe body, the user interface configured for deactivating the stimulation circuitry.

Aspect 62. The transvaginal stimulation device of any of aspects 39 to 60, further comprising an extraction element extending proximally from the probe body configured for being grasped to extract the probe body from the vaginal cavity of the female patient.

Aspect 63. The transvaginal stimulation device of aspect 62, wherein the extraction mechanism comprises a fingerhold having a proximal surface configured for approximating a pubic bone of the female patient when the probe body is fully disposed in the vaginal cavity.

Aspect 64. The transvaginal stimulation device of any of aspects 39 to 60, further comprising a pair of linear electrode arrays extending along the length of the probe body, the pair of linear electrode arrays respectively comprising the pair of electrodes.

Aspect 65. The transvaginal stimulation device of aspect 64, wherein different subsets of electrodes of the respective pair of electrodes arrays are configured for being selectively activated.

Aspect 66. The transvaginal stimulation device of aspect 65, wherein the different subsets of electrodes comprise different bipolar pairs of electrodes.

Aspect 67. The transvaginal stimulation device of aspect 66, wherein the different bipolar pairs of electrodes are transverse bipolar pairs of electrodes.

Aspect 68. The transvaginal stimulation device of aspect 66, wherein the different bipolar pairs of electrodes are longitudinal bipolar pairs of electrodes.

Aspect 69. The transvaginal stimulation device of any of aspects 65 to 67, wherein the different subsets of electrodes are configured for being cyclically activated one-at-a-time.

Aspect 70. The transvaginal stimulation device of any of aspects 39-69, wherein a proximal region of the probe body comprises shoulders that laterally taper inward in a proximal direction to form a waist.

Aspect 71. The transvaginal stimulation device of aspects 70, wherein an axial center of the pair of electrodes is distally spaced from the waist a distance in a range between 1.5 cm and 2.5 cm.

Aspect 72. The transvaginal stimulation device of aspect 70, wherein the probe body comprises telescoping proximal and distal probe bodies configured for being axially displaced relative to each other, such that a distance between the pair of electrodes and the waist of the probe body can be varied.

Aspect 73. The transvaginal stimulation device of aspect 70, wherein the pair of electrodes is configured for being axially displaced relative to the probe body, such that a distance between the pair of electrodes and the waist of the probe body can be varied.

Aspect 74. A transvaginal stimulation system, comprising: the transvaginal stimulation device of any of aspects 39 to 73; and a clinician programmer configured for wirelessly programming the transvaginal stimulation device.

Aspect 75. The transvaginal stimulation system of aspect 74, wherein the transvaginal stimulation device further comprises a pair of linear arrays of electrodes respectively comprising the pair of electrodes, the pair of linear electrode arrays respectively extending along length of the probe body, and the clinician programmer is configured for: determining a stimulation regimen by selectively activating different pairs of electrodes respectively in the linear electrode arrays; and programming the transvaginal stimulation device with the stimulation regimen, such that the transvaginal stimulation device is configured for conveying electrical stimulation energy between the pair of electrodes in accordance with the stimulation regimen.

Aspect 76. The transvaginal stimulation system of aspect 74 or 75, further comprising a patient control configured for wirelessly controlling operation of the transvaginal stimulation device.

Aspect 77. An intravaginal device, comprising: a probe body sized to fit entirely within a vaginal cavity of a female patient, the probe body having a length extending in a longitudinal direction, a width extending in a lateral direction, and a depth being perpendicular to the length and width, the probe body having a stimulating side defined by the length and the width of the probe body; an extraction mechanism including an elongated tail member affixed to the proximal region of the probe body; and a pair of electrodes disposed on the stimulating side of the probe body and laterally spaced from each other.

Aspect 78. The transvaginal stimulation device of aspect 77, wherein the probe body has a concave region longitudinally extending along the stimulating side of the probe body, and wherein the concave region is shaped to cradle a urethra carina of the female patient when the probe body is positioned in the vaginal cavity.

Aspect 79. The transvaginal stimulation device of aspect 77 or 78, wherein the probe body is rigid or semi-rigid.

Aspect 80. The transvaginal stimulation device of any of aspects 77 to 79, wherein the length of the probe body is in a range between 4 cm and 8 cm.

Aspect 81. The transvaginal stimulation device of any of aspects 77 to 80, wherein the width of the probe body has a greatest lateral extent that is greater than the depth of the probe body.

Aspect 82. The transvaginal stimulation device of any of aspects 77 to 81, wherein a distal region of the probe body laterally flares outward in a distal direction from a mid-region of the probe body to form a flattened scoop that angles away from the stimulating side of the probe body.

Aspect 83. The transvaginal stimulation device of aspect 82, wherein a proximal region of the probe body laterally flares outward in a proximal direction from the mid-region to form shoulders.

Aspect 84. The transvaginal stimulation device of aspect 83, wherein the mid-region of the probe body is sized and configured, such that when the probe body is fully disposed in the vaginal cavity, levator ani muscles of the female patient are disposed adjacent to the mid-region between the flattened scoop and the shoulders.

Aspect 85. The transvaginal stimulation device of any of aspects 77 to 84, wherein the transvaginal stimulation device is free of any electrodes laterally disposed relative to the pair of electrodes.

Aspect 86. The transvaginal stimulation device of any of aspects 77 to 85, wherein the probe body has a non-stimulating side opposite the stimulating side of the probe body, wherein the non-stimulating side of the probe body is free of any electrode.

Aspect 87. The transvaginal stimulation device of any of aspects 77 to 86, wherein the pair of electrodes is a transverse pair of electrodes.

Aspect 88. The transvaginal stimulation device of aspect 87, wherein the pair of electrodes each have an elongated shape and are disposed parallel to each other.

Aspect 89. The transvaginal stimulation device of aspect 88, wherein the pair of electrodes respectively have lengths extending along the length of the probe body in a range between 4 mm and 12 mm.

Aspect 90. The transvaginal stimulation device of any of aspects 87 to 89, wherein the pair of electrodes have an edge-to-edge lateral spacing in a range between 10 mm and 20 mm.

Aspect 91. The transvaginal stimulation device of any of aspects 87 to 90, wherein the pair of electrodes includes a first electrode having a first flat tissue contacting surface and a second electrode having a second flat tissue contacting surface tissue.

Aspect 92. The transvaginal stimulation device of aspect 91, wherein the first tissue contacting surface and the second tissue contacting surface form an angle within a range between 160° and 200°.

Aspect 93. The transvaginal stimulation device of aspect 91, wherein the first tissue contacting surface and the second tissue contacting surface form an angle within a range between 170° and 190°.

Aspect 94. The transvaginal stimulation device of aspect 91, wherein the first tissue contacting surface and the second tissue contacting surface form an angle of 180°.

Aspect 95. The transvaginal stimulation device of any of aspects 77 to 94, wherein the pair of electrodes are respectively positioned on the probe body, so that when the probe body is positioned in the vaginal cavity, bipolar electrical stimulation energy delivered between the pair of electrodes stimulates at least one muscle of a urethral sphincter of the female patient without substantially stimulating pelvic floor muscles of the female patient.

Aspect 96. The transvaginal stimulation device of aspect 95, wherein the at least one muscle of the urethral sphincter comprises a mid-urethral striated sphincter muscle.

Aspect 97. The transvaginal stimulation device of aspect 95 or 96, wherein the at least one muscle of the urethral sphincter comprises one or both of a circumferential smooth muscle and a longitudinal smooth muscle.

Aspect 98. The transvaginal stimulation device of any of aspects 77 to 97, further comprising stimulation circuitry contained within the probe body, the stimulation circuitry configured for delivering bipolar electrical stimulation energy between the pair of electrodes.

Aspect 99. The transvaginal stimulation device of aspect 98, further comprising a user interface disposed on the probe body, the user interface configured for deactivating the stimulation circuitry.

Aspect 100. The transvaginal stimulation device of any of aspects 77 to 99, wherein the extraction mechanism comprises a fingerhold having a proximal surface configured for approximating a pubic bone of the female patient when the probe body is fully disposed in the vaginal cavity of the female patient.

Aspect 101. The transvaginal stimulation device of any of aspects 77 to 100, further comprising a pair of linear electrode arrays extending along the length of the probe body, the pair of linear electrode arrays respectively comprising the pair of electrodes.

Aspect 102. The transvaginal stimulation device of aspect 101, wherein different subsets of electrodes of the respective pair of electrodes arrays are configured for being selectively activated.

Aspect 103. The transvaginal stimulation device of aspects 102, wherein the different subsets of electrodes comprise different bipolar pairs of electrodes.

Aspect 104. The transvaginal stimulation device of aspects 103, wherein the different bipolar pairs of electrodes are transverse bipolar pairs of electrodes.

Aspect 105. The transvaginal stimulation device of aspects 103, wherein the different bipolar pairs of electrodes are longitudinal bipolar pairs of electrodes.

Aspect 106. The transvaginal stimulation device of any of aspects 102 to 105, wherein the different subsets of electrodes are configured for being cyclically activated one-at-a-time.

Aspect 107. The transvaginal stimulation device of any of aspects 77 to 100, wherein a proximal region of the probe body comprises shoulders that laterally taper inward in a proximal direction to form a waist.

Aspect 108. The transvaginal stimulation device of aspect 107, wherein an axial center of the pair of electrodes is distally spaced from the waist a distance in a range between 1.5 cm and 2.5 cm.

Aspect 109. The transvaginal stimulation device of aspect 107, wherein the probe body comprises telescoping proximal and distal probe bodies configured for being axially displaced relative to each other, such that a distance between the pair of electrodes and the waist of the probe body can be varied.

Aspect 110. The transvaginal stimulation device of aspect 107, wherein the pair of electrodes is configured for being axially displaced relative to the probe body, such that a distance between the pair of electrodes and the waist of the probe body can be varied.

Aspect 111. A transvaginal stimulation system, comprising: the transvaginal stimulation device of any of aspects 77 to 110; and a clinician programmer configured for wirelessly programming the transvaginal stimulation device.

Aspect 112. The transvaginal stimulation system of aspect 111, wherein the transvaginal stimulation device further comprises a pair of linear arrays of electrodes respectively comprising the pair of electrodes, the pair of linear electrode arrays respectively extending along length of the probe body, and the clinician programmer is configured for: determining a stimulation regimen by selectively activating different pairs of electrodes respectively in the linear electrode arrays; and programming the transvaginal stimulation device with the stimulation regimen, such that the transvaginal stimulation device is configured for conveying electrical stimulation energy between the pair of electrodes in accordance with the stimulation regimen.

Aspect 113. The transvaginal stimulation system of any of aspects 77 to 112, further comprising a patient control configured for wirelessly controlling operation of the transvaginal stimulation device.

Aspect 114. A transvaginal stimulation device, comprising: a probe body sized to fit entirely within a vaginal cavity of a female patient, the probe body having a length extending in a longitudinal direction, a width extending in a lateral direction, and a depth being perpendicular to the length and width, the probe body having a stimulating side defined by the length and the width of the probe body; and a transverse pair of electrodes disposed on the stimulating side of the probe body and laterally spaced from each other, wherein the pair of electrodes includes a first electrode having a first flat tissue contacting surface and a second electrode having a second flat tissue contacting surface tissue that forms an angle with the first tissue contact surface within a range between 160° and 200°.

Aspect 115. The transvaginal stimulation device of aspect 114, wherein the probe body has a concave region longitudinally extending along the stimulating side of the probe body, and wherein the concave region is shaped to cradle a urethra carina of the female patient when the probe body is positioned in the vaginal cavity. Optionally, the probe body may be rigid or semi-rigid.

Aspect 116. The transvaginal stimulation device of aspect 114 or 115, wherein the length of the probe body is in a range between 4 cm and 8 cm.

Aspect 117. The transvaginal stimulation device of any of aspects 114 to 116, wherein the width of the probe body has a greatest lateral extent that is greater than the depth of the probe body.

Aspect 118. The transvaginal stimulation device of any of aspects 114 to 117, wherein a distal region of the probe body laterally flares outward in a distal direction from a mid-region of the probe body to form a flattened scoop that angles away from the stimulating side of the probe body.

Aspect 119. The transvaginal stimulation device of aspect 118, wherein a proximal region of the probe body laterally flares outward in a proximal direction from the mid-region to form shoulders. Optionally, the mid-region of the probe body is sized and configured, such that when the probe body is fully disposed in the vaginal cavity, levator ani muscles of the female patient are disposed adjacent to the mid-region between the flattened scoop and the shoulders.

Aspect 120. The transvaginal stimulation device of any of aspect 114 to 120, wherein the transvaginal stimulation device is free of any electrodes laterally disposed relative to the pair of electrodes.

Aspect 121. The transvaginal stimulation device of any of aspects 114 to 120, wherein the probe body has a non-stimulating side opposite the stimulating side of the probe body, wherein the non-stimulating side of the probe body is free of any electrode.

Aspect 122. The transvaginal stimulation device of any of aspects 114 to 120, wherein the pair of electrodes each have an elongated shape and are disposed parallel to each other.

Aspect 123. The transvaginal stimulation device of any of aspects 114 to 122, wherein the pair of electrodes respectively have lengths extending along the length of the probe body in a range between 4 mm and 12 mm.

Aspect 124. The transvaginal stimulation device of any of aspects 122 to 123, wherein the pair of electrodes have an edge-to-edge lateral spacing in a range between 10 mm and 20 mm.

Aspect 125. The transvaginal stimulation device of any of aspects 114 to 124, wherein the first tissue contacting surface and the second tissue contacting surface form an angle within a range between 170° and 190°.

Aspect 126. The transvaginal stimulation device of any of aspects 114 to 125, wherein the first tissue contacting surface and the second tissue contacting surface form an angle of 180°.

Aspect 127. The transvaginal stimulation device of any of aspects 114 to 126, wherein the pair of electrodes are respectively positioned on the probe body, so that when the probe body is positioned in a vaginal cavity of the female patient, bipolar electrical stimulation energy delivered between the pair of electrodes stimulates at least one muscle of a urethral sphincter of the female patient without substantially stimulating pelvic floor muscles of the female patient.

Aspect 128. The transvaginal stimulation device of aspect 127, wherein the at least one muscle of the urethral sphincter comprises a mid-urethral striated sphincter muscle.

Aspect 129. The transvaginal stimulation device of aspect 127 or 128, wherein the at least one muscle of the urethral sphincter comprises one or both of a circumferential smooth muscle and a longitudinal smooth muscle.

Aspect 130. The transvaginal stimulation device of any of aspects 114 to 129, further comprising stimulation circuitry contained within the probe body, the stimulation circuitry configured for delivering bipolar electrical stimulation energy between the pair of electrodes. Optionally, the transvaginal stimulation device may further comprise a user interface disposed on the probe body, the user interface configured for deactivating the stimulation circuitry.

Aspect 131. The transvaginal stimulation device of any of aspects 114 to 130, further comprising an extraction element extending proximally from the probe body configured for being grasped to extract the probe body from the vaginal cavity of the female patient. Without limitation, the extraction mechanism may comprise a fingerhold having a proximal surface configured for approximating a pubic bone of the female patient when the probe body is fully disposed in the vaginal cavity.

Aspect 132. The transvaginal stimulation device of any of aspects 114 to 131, further comprising a pair of linear electrode arrays extending along the length of the probe body, the pair of linear electrode arrays respectively comprising the pair of electrodes. Without limitation, different subsets of electrodes of the respective pair of electrodes arrays may be configured for being selectively activated. Without limitation, the different subsets of electrodes may comprise different bipolar pairs of electrodes, which may optionally be transverse bipolar pairs of electrodes or longitudinal bipolar pairs of electrodes. Without limitation, the different subsets of electrodes may be configured for being cyclically activated one-at-a-time.

Aspect 133. The transvaginal stimulation device of any of aspects 114 to 131, wherein a proximal region of the probe body comprises shoulders that laterally taper inward in a proximal direction to form a waist. Optionally, an axial center of the pair of electrodes may be distally spaced from the waist a distance in a range between 1.5 cm and 2.5 cm. Optionally, the probe body may comprise telescoping proximal and distal probe bodies configured for being axially displaced relative to each other, such that a distance between the pair of electrodes and the waist of the probe body can be varied. Optionally, the pair of electrodes may be configured for being axially displaced relative to the probe body, such that a distance between the pair of electrodes and the waist of the probe body can be varied.

Aspect 134. A transvaginal stimulation system, comprising: the transvaginal stimulation device of any of aspects 114 to 133; and a clinician programmer configured for wirelessly programming the transvaginal stimulation device. The transvaginal stimulation system may optionally further include a pair of linear arrays of electrodes respectively comprising the pair of electrodes, the pair of linear electrode arrays respectively extending along length of the probe body, in which case the clinician programmer may be configured for: determining a stimulation regimen by selectively activating different pairs of electrodes respectively in the linear electrode arrays; and programming the transvaginal stimulation device with the stimulation regimen, such that the transvaginal stimulation device is configured for conveying electrical stimulation energy between the pair of electrodes in accordance with the stimulation regimen. Optionally, the transvaginal stimulation system may further include a patient control configured for wirelessly controlling operation of the transvaginal stimulation device.

Aspect 135. A method for treating stress urinary incontinence in a female patient using a transvaginal stimulation device comprising a probe body and a pair of electrodes disposed on the probe body, the method comprising: inserting the intravaginal device into a vaginal cavity of the female patient; positioning the pair of electrodes against an anterior wall of the vagina of the female patient; and conveying stimulation energy between the pair of electrodes to stimulate at least one muscle of a urethral sphincter muscle of the female patient without substantially stimulating pelvic floor muscles of the female patient. Optionally, the probe body may be provided with a concave region longitudinally extending along the probe body, wherein the method may further comprise cradling a urethra carina of the female patient when the probe body is inserted in the vaginal cavity. Optionally, the probe body may be rigid or semi-rigid.

Aspect 136. The method of aspect 135, wherein the length of the probe body is in a range between 4 cm and 8 cm.

Aspect 137. The method of aspect 135 or 136, wherein the width of the probe body has a greatest lateral extent that is greater than the depth of the probe body, thereby preventing rotation of the probe body relative to the vaginal cavity.

Aspect 138. The method of any of aspects 135 to 137, wherein a distal region of the probe body laterally flares outward in a distal direction from mid-region in the lateral direction to form a flattened scoop, and a proximal region of the probe body laterally flares outward in a proximal direction from the mid-region to form shoulders, wherein the levator ani muscles of the female patient are disposed adjacent to the mid-region between the flattened scoop and the shoulders when the probe body is fully disposed in the vaginal cavity. Optionally, the flattened scoop angles away from the stimulating side of the probe body, such that the flattened scoop conforms to a posteriorly angled cranial end of the vaginal cavity when the probe body is fully disposed in the vaginal cavity.

Aspect 139. The method of any of aspects 135 to 138, wherein the stimulation energy is unidirectionally conveyed through an anterior wall of a vagina of the female patient to stimulate the urethral sphincter muscle of the female patient without substantially stimulating pelvic floor muscles of the female patient.

Aspect 140. The method of any of aspects 135 to 139, wherein the stimulation energy is transverse bipolar stimulation energy. Optionally, the pair of electrodes may each have an elongated shape and are disposed parallel to each other. Optionally, each electrode of the pair of electrodes respectively may have a length extending along the length of the probe body in a range between 4 mm and 12 mm. Optionally, the pair of electrodes may have an edge-to-edge lateral spacing in a range between 5 mm and 25 mm. Optionally, the pair of electrodes may have an edge-to-edge lateral spacing in a range between 10 mm and 20 mm. Optionally, the pair of electrodes includes a first electrode having a first flat tissue contacting surface and a second electrode having a second flat tissue contacting surface tissue, wherein the first tissue contacting surface and the second tissue contacting surface form an angle within a range between 160° and 200°, an angle within a range between 170° and 190°, or an angle of 180°.

Aspect 141. The method of any of aspects 135 to 140, wherein the at least one muscle of the urethral sphincter comprises a mid-urethral striated sphincter muscle.

Aspect 142. The method of any of aspects 135 to 141, wherein the at least one muscle of the urethral sphincter comprises one or both of a circumferential smooth muscle and a longitudinal smooth muscle.

Aspect 143. The method of any of aspects 135 to 142, wherein the stimulation energy is delivered by stimulation circuitry contained within the probe body.

Aspect 144. The method of any of aspects 135 to 143, further comprising terminating the stimulation energy conveyed between the electrodes by actuating a user interface disposed on the probe body.

Aspect 145. The method of any of aspects 135 to 144, further comprising extracting the probe body from the vaginal cavity by grasping an extraction element extending proximally from the probe body. Optionally, the extraction mechanism may comprise a fingerhold having a proximal surface, in which case the method may further comprise approximating the pubic bone of the female patient when the probe body is fully disposed in the vaginal cavity.

Aspect 146. The method of any of aspects 135 to 145, further comprising: measuring a urethral closing pressure of the female patient while applying the stimulation energy to the urethral sphincter muscle of the female patient in accordance with a stimulation regimen; and controlling the stimulation regimen in response to the measured urethral closing pressure. Without limitation, controlling the stimulation regimen may comprise determining a stimulation regimen by selectively activating different pairs of electrodes arranged in a pair of linear electrode arrays extending along the length of the probe body, and programming the transvaginal stimulation device with the stimulation regimen, such that the transvaginal stimulation device is configured for conveying the electrical stimulation energy between the pair of electrodes in accordance with the stimulation regimen. Optionally, the different pairs of electrodes may be transverse bipolar pairs of electrodes or longitudinal bipolar pairs of electrodes. Optionally, the method may further comprise cyclically conveying stimulation energy between the different pairs of electrodes one-at-a-time to stimulate the at least one muscle of the urethral sphincter muscle of the female patient without substantially stimulating pelvic floor muscles of the female patient.

Aspect 147. The method of any of aspects 135 to 146, further comprising mechanically fitting the transvaginal stimulation device to the female patient. Without limitation, mechanically fitting the transvaginal stimulation device to the female patient may comprise axially displacing the pair of electrodes relative to the probe body to vary a distance between the pair of electrodes and the waist of the probe body. Alternatively, mechanically fitting the transvaginal stimulation device to the female patient may comprise inserting a plurality of different intravaginal stimulation devices into the vaginal cavity, the transvaginal stimulation devices having different distances between a pair of electrodes and waists of the probe bodies of the transvaginal stimulation devices, and selecting the intravaginal stimulation devices from the plurality of different intravaginal stimulation devices. Without limitation, a proximal region of the probe body may comprise shoulders that laterally taper inward in a proximal direction to form a waist, wherein an axial center of the pair of electrodes is distally spaced from the waist a distance in the range of 1.5 cm-2.5 cm. Alternatively, and without limitation, the probe body may comprise telescoping proximal and distal probe bodies, wherein mechanically fitting the transvaginal stimulation to the female patient comprises axially displacing the telescoping probe bodies relative to each other to vary a distance between the pair of electrodes and the waist of the probe body.

Aspect 148. The method of any of aspects 135 to 147, further comprising wirelessly controlling operation of the transvaginal stimulation device via a patient control device.

The invention claimed is:

1. A transvaginal stimulation device, comprising:
a probe body sized to fit entirely within a vaginal cavity of a female patient, the probe body having a length extending in a longitudinal direction, a width extending in a lateral direction, and a depth extending perpendicular to the length and width, the probe body having a stimulating side defined by the length and the width of the probe body, the probe body having a concave region longitudinally extending along the stimulating side of the probe body; and
a pair of electrodes disposed on the stimulating side of the probe body and laterally spaced from each other, such that the concave region is entirely disposed between outer edges of the pair of electrodes, wherein
the probe body has a non-stimulating side opposite the stimulating side that is completely free of electrodes.

2. The transvaginal stimulation device of claim 1, wherein the concave region is shaped to cradle a urethra carina of the female patient when the probe body is positioned in a vaginal cavity of the female patient.

3. The transvaginal stimulation device of claim 1, wherein a distal region of the probe body laterally flares outward in a distal direction from a mid-region of the probe body to form a flattened scoop, and wherein a proximal region of the probe body laterally flares outward in a proximal direction from the mid-region to form shoulders.

4. The transvaginal stimulation device of claim 3, wherein the mid-region of the probe body is sized and configured, such that when the probe body is fully disposed in the vaginal cavity, levator ani muscles of the female patient are disposed adjacent to the mid-region between the flattened scoop and the shoulders.

5. The transvaginal stimulation device of claim 1, wherein the pair of electrodes is a transverse pair of electrodes.

6. The transvaginal stimulation device of claim 5, wherein the pair of electrodes have an edge-to-edge lateral spacing in a range between 5 mm and 25 mm.

7. The transvaginal stimulation device of claim 5, wherein the pair of electrodes have an edge-to-edge lateral spacing in a range of between 10 mm and 20 mm.

8. The transvaginal stimulation device of claim 5, wherein the pair of electrodes are disposed along a same plane.

9. The transvaginal stimulation device of claim 1, wherein the pair of electrodes are positioned on the probe body, so that when the probe body is positioned in the vaginal cavity, bipolar electrical stimulation energy delivered between the pair of electrodes stimulates at least one muscle of a urethral sphincter of the female patient without substantially stimulating pelvic floor muscles of the female patient.

10. The transvaginal stimulation device of claim 1, further comprising:
stimulation circuitry contained within the probe body, the stimulation circuitry configured for delivering bipolar electrical stimulation energy between the pair of electrodes; and a user interface disposed on the probe body, the user interface configured for deactivating the stimulation circuitry.

11. The transvaginal stimulation device of claim 1, wherein a proximal region of the probe body comprises shoulders that laterally taper inward in a proximal direction to form a waist, and wherein the probe body comprises telescoping proximal and distal probe bodies configured for being axially displaced relative to each other, such that a distance between the pair of electrodes and the waist of the probe body can be varied.

12. The transvaginal stimulation device of claim 1, wherein a proximal region of the probe body comprises shoulders that laterally taper inward in a proximal direction to form a waist, and wherein the pair of electrodes is configured for being axially displaced relative to the probe body, such that a distance between the pair of electrodes and the waist of the probe body can be varied.

13. A transvaginal stimulation system, comprising:
the transvaginal stimulation device of claim 1;
a clinician programmer configured for wirelessly programming the transvaginal stimulation device; and
a patient control configured for wirelessly controlling operation of the transvaginal stimulation device.

14. A transvaginal stimulation device, comprising:
a probe body sized to fit entirely within a vaginal cavity of a female patient, the probe body having a length extending in a longitudinal direction, a width extending in a lateral direction, and a depth extending perpendicular to the length and width, the probe body having a stimulating side defined by the length and the width of the probe body, the probe body having a pair of convex regions longitudinally extending along the stimulating side of the probe body; and
a pair of electrodes disposed on respective peaks of the pair of convex regions of the probe body and laterally spaced from each other, wherein
the probe body has a non-stimulating side opposite the stimulating side that is completely free of electrodes.

15. A transvaginal stimulation device, comprising:
a probe body sized to fit entirely within a vaginal cavity of a female patient, the probe body having a length extending in a longitudinal direction, a width extending in a lateral direction, and a depth extending perpendicular to the length and width, the probe body having a stimulating side defined by the length and the width of the probe body; and
a pair of electrodes disposed along a same plane on the stimulating side of the probe body and laterally spaced from each other, wherein
the probe body has a non-stimulating side opposite the stimulating side that is completely free of electrodes.

* * * * *